United States Patent
De Haard et al.

(10) Patent No.: US 11,712,468 B2
(45) Date of Patent: Aug. 1, 2023

(54) CD70 COMBINATION THERAPY

(71) Applicants: Argenx BV, Ghent (BE); University of Bern, Bern (CH)

(72) Inventors: Johannes De Haard, Ghent (BE); Samson Fung, Ghent (BE); Nicolas Leupin, Ghent (BE); Adrian Ochsenbein, Ghent (BE); Carsten Riether, Ghent (BE); Luc Van Rompaey, Ghent (BE)

(73) Assignees: ARGENX BV, Ghent (BE); University of Bern, Bern (CH)

( * ) Notice: Subject to any disclaimer, the term of this patent is extended or adjusted under 35 U.S.C. 154(b) by 269 days.

(21) Appl. No.: 16/719,220

(22) Filed: Dec. 18, 2019

(65) Prior Publication Data

US 2020/0222532 A1 Jul. 16, 2020

(30) Foreign Application Priority Data

Dec. 18, 2018 (GB) .................................... 1820582
Aug. 1, 2019 (GB) .................................... 1911007
Dec. 4, 2019 (GB) .................................... 1917701

(51) Int. Cl.
| | |
|---|---|
| *A61K 39/395* | (2006.01) |
| *A61K 31/496* | (2006.01) |
| *A61K 31/706* | (2006.01) |
| *A61K 45/06* | (2006.01) |
| *A61K 39/00* | (2006.01) |
| *A61P 35/00* | (2006.01) |

(52) U.S. Cl.
CPC ........ *A61K 39/3955* (2013.01); *A61K 31/496* (2013.01); *A61K 31/706* (2013.01); *A61K 45/06* (2013.01); *A61P 35/00* (2018.01); *A61K 2039/505* (2013.01); *A61K 2039/545* (2013.01)

(58) Field of Classification Search
CPC .............. A61K 39/3955; A61K 31/496; A61K 31/706; A61K 45/06; A61K 2039/505; A61K 2039/545; A61K 2300/00; A61P 35/00; C07D 471/04; C07K 16/2875
See application file for complete search history.

(56) References Cited

U.S. PATENT DOCUMENTS

| | | |
|---|---|---|
| 5,573,924 A | 11/1996 | Beckmann et al. |
| 5,859,205 A | 1/1999 | Adair et al. |
| 6,500,633 B1 | 12/2002 | Compton |
| 6,844,422 B1 | 1/2005 | Niehrs et al. |
| 7,261,892 B2 | 8/2007 | Terrett |
| 7,491,390 B2 | 2/2009 | Law et al. |
| 7,641,903 B2 | 1/2010 | Law et al. |
| 7,662,387 B2 | 2/2010 | Law et al. |
| 7,723,477 B2 | 5/2010 | Gurney et al. |
| 7,728,114 B2 | 6/2010 | Mach et al. |
| 7,745,156 B2 | 6/2010 | Terrett |
| 7,745,419 B2 | 6/2010 | Oh et al. |
| 7,982,013 B2 | 7/2011 | Gurney et al. |
| 8,124,738 B2 | 2/2012 | Terret et al. |
| 8,324,361 B2 | 12/2012 | Gurney et al. |
| 8,455,622 B2 | 6/2013 | McDonagh et al. |
| 8,507,442 B2 | 8/2013 | Gurney et al. |
| 8,535,678 B2 | 9/2013 | Law et al. |
| 8,552,156 B2 | 10/2013 | Takayanagi et al. |
| 8,604,052 B2 | 12/2013 | Hood et al. |
| 8,647,623 B2 | 2/2014 | Takayanagi et al. |
| 8,663,642 B2 | 3/2014 | Law et al. |
| 8,765,913 B2 | 7/2014 | Gurney et al. |
| 8,834,882 B2 | 9/2014 | Silence et al. |
| 8,841,418 B2 | 9/2014 | Karsunky et al. |
| 9,556,270 B2 | 1/2017 | Takayanagi et al. |
| 9,605,070 B2 | 3/2017 | Sabatos-Peyton et al. |
| 9,631,026 B2 | 4/2017 | Karsunky et al. |
| 2003/0148321 A1 | 8/2003 | Pecker |

(Continued)

FOREIGN PATENT DOCUMENTS

| | | |
|---|---|---|
| WO | WO 1994/005691 A1 | 3/1994 |
| WO | WO 2003/046581 A2 | 6/2003 |

(Continued)

OTHER PUBLICATIONS

DiNardo; Safety and preliminary efficacy of venetoclax with decitabine orazactidine in elderly patients with previously untreated acute myeloid leukemia: a non-randomized, open-label, phase 1b study, The Lancet, vol. 19, 2018) (Year: 2018).*
Argenx [online], 2017, "ARGX-110", https://web.archive.org/web/20170505150651/www.argenx.com:80/en-GB/content/argx-110/18/ [accessed May 5, 2017].
Arroyo Hornero et al., "CD70 expression determines the therapeutic efficacy of expanded human regulatory T cells", Communications Biology, 2020, vol. 3, No. 375, pp. 1-17.

(Continued)

*Primary Examiner* — Laura B Goddard
*Assistant Examiner* — Sarah A Alsomairy
(74) *Attorney, Agent, or Firm* — Dechert LLP; Andrew T. Wilkins; Kayla L. Metzger

(57) ABSTRACT

The present invention provides combinations and methods using same for the treatment of malignancy, particularly a myeloid malignancy such as acute myeloid leukemia (AML), myelodysplastic syndromes (MDS), myeloproliferative neoplasms (MPN), chronic myeloid leukemia (CML), and chronic myelomonocytic leukemia (CMML). The combination may comprise an antibody or antigen-binding fragment thereof that binds to CD70, and an inhibitor of BCL-2. In certain embodiments, the antibody is ARGX-110 (cusatuzumab). In certain embodiments, the BCL-2 inhibitor is venetoclax. In certain embodiments, the combination provides synergistic treatment of AML. The combination may additionally comprise at least one additional anti-cancer agent.

36 Claims, 10 Drawing Sheets

Specification includes a Sequence Listing.

(56) References Cited

U.S. PATENT DOCUMENTS

| | | |
|---|---|---|
| 2005/0118656 A1 | 6/2005 | Terrett |
| 2006/0115832 A1 | 6/2006 | Hoon |
| 2006/0275844 A1 | 12/2006 | Linke |
| 2007/0072178 A1 | 3/2007 | Haferlach |
| 2008/0025989 A1 | 1/2008 | Law et al. |
| 2008/0138341 A1 | 6/2008 | Law et al. |
| 2008/0280297 A1 | 11/2008 | Dalla-Favera |
| 2009/0028872 A1 | 1/2009 | Terret et al. |
| 2009/0074772 A1 | 3/2009 | Law et al. |
| 2009/0148942 A1 | 6/2009 | McDonagh et al. |
| 2009/0232806 A1 | 9/2009 | Law et al. |
| 2010/0129362 A1 | 5/2010 | Law et al. |
| 2010/0015891 A1 | 6/2010 | Law et al. |
| 2010/0150925 A1 | 6/2010 | Law et al. |
| 2010/0150950 A1 | 6/2010 | Coccia et al. |
| 2010/0183636 A1 | 7/2010 | Law et al. |
| 2010/0267626 A1 | 10/2010 | Cheung et al. |
| 2010/0278779 A1 | 11/2010 | Zeldis |
| 2011/0190157 A1 | 8/2011 | Kipps |
| 2012/0093805 A1 | 4/2012 | Kubota |
| 2012/0178111 A1 | 7/2012 | Diamandis |
| 2013/0078237 A1 | 3/2013 | Delaney et al. |
| 2013/0243795 A1 | 9/2013 | Chen et al. |
| 2014/0141016 A1 | 5/2014 | Silence et al. |
| 2014/0147450 A1 | 5/2014 | Silence et al. |
| 2014/0235843 A1 | 8/2014 | Silence et al. |
| 2015/0086521 A1 | 3/2015 | Godfrin |
| 2015/0132324 A1 | 5/2015 | Cong et al. |
| 2018/0244792 A1 | 8/2018 | Duncan et al. |
| 2019/0106498 A1* | 4/2019 | de Haard ............... A61P 35/02 |
| 2020/0222532 A1 | 7/2020 | De Haard |

FOREIGN PATENT DOCUMENTS

| | | |
|---|---|---|
| WO | WO 2004/073656 A2 | 9/2004 |
| WO | WO 2006/044643 A2 | 4/2006 |
| WO | WO 2006/113909 A2 | 10/2006 |
| WO | WO 2007/038637 A2 | 4/2007 |
| WO | WO 2007/146968 A2 | 12/2007 |
| WO | WO 2008/074004 A2 | 6/2008 |
| WO | WO 2010/001251 A2 | 1/2010 |
| WO | WO 2010/014948 A1 | 2/2010 |
| WO | WO 2012/098407 A2 | 7/2012 |
| WO | WO 2012/123586 A1 | 9/2012 |
| WO | WO 2013/093508 A2 | 6/2013 |
| WO | WO 2013/177420 A2 | 11/2013 |
| WO | WO 2013/185353 A1 | 12/2013 |
| WO | WO 2014/045101 A1 | 3/2014 |
| WO | WO 2014/100772 A2 | 6/2014 |
| WO | WO 2015/138600 A2 | 9/2015 |
| WO | WO 2016/111947 A2 | 7/2016 |
| WO | WO 2017/079116 A1 | 5/2017 |
| WO | WO 2017/134140 A1 | 8/2017 |
| WO | WO 2017/021354 A1 | 9/2017 |
| WO | WO 2017/160954 A1 | 9/2017 |
| WO | WO-2017160954 A1 * | 9/2017 ....... A61K 39/39558 |
| WO | WO 2018/229303 A1 | 12/2018 |
| WO | WO 2019/141732 A1 | 7/2019 |
| WO | WO-2019141732 A1 * | 7/2019 ........... A61K 9/0019 |

OTHER PUBLICATIONS

Baba et al., "Highly Enhanced Expression of CD70 on Human T-Lymphotropic Virus Type 1-Carrying T-Cell Lines and Adult T-Cell Leukemia Cells", Journal of Virology, Apr. 2008, pp. 3843-3852.

Barthelemy et al., "Comprehensive Analysis of the Factors Contributing to the Stability and Solubility of Autonomous Human VH Domains", Journal of Biological Chemistry, 2008, 283: 3639-3654.

Baxevanis, "Antibody-based cancer therapy", Expert Opinion: Drug Discovery, 2008, vol. 3, No. 4, pp. 441-452.

Beiboer et al., "Guided selection of a pan carcinoma specific antibody reveals similar binding characteristics yet structural divergence between the original murine antibody and its human equivalent", Journal of Molecular Biology, 2000, 296(3): 833-849.

Brugnoni et al., "CD70 expression on T-cell subpopulations: study of normal individuals and patients with chronic immune activation", Immunology Letters, 1997, vol. 55, pp. 99-104.

CAS Registry No. 0641571-10-0. [Last Accessed Dec. 16, 2016].
CAS Registry No. 1165740-62-4. [Last Accessed Dec. 16, 2016].
CAS Registry No. 302962-49-8. [Last Accessed Dec. 16, 2016].
CAS Registry No. 379231-04-6. [Last Accessed Dec. 16, 2016].
CAS Registry No. 380843-75-4. [Last Accessed Dec. 16, 2016].
CAS Registry No. 639089-54-6. [Last Accessed Dec. 16, 2016].
CAS Registry No. 664993-53-7. [Last Accessed Dec. 16, 2016].
CAS Registry No. 82115-62-6. [Last Accessed Dec. 16, 2016].
CAS Registry No. 859212-16-1. [Last Accessed Dec. 16, 2016].
CAS Registry No. 943319-70-8. [Last Accessed Dec. 16, 2016].

Choi et al., "Predicting antibody complementarity determining region structures without classification", Molecular BioSystems, 2011, 7(12): 3327-3334.

Clinicaltrials.Gov, "A Study of ARGX-110 in Combination with Azacytidine in Participants with Newly Diagnosed Acute Myeloid Leukemia (AML) or High Risk Myelodysplastic Syndrome (MDS)", ClinicalTrials.gov Identifier No. NCT03030612, Jan. 25, 2017.

Colman, "Effects of amino acid sequence changes on antibody-antigen interactions", Research in Immunology, 1994, vol. 145, pp. 33-36.

Combined Search and Examination Report dated Feb. 8, 2019 in related Application No. GB1709677.7 (4 pages).

De Genst et al., "Antibody repertoire development in camelids", Developmental and Comparative Immunology, 30 (2006); 187-198.

Denoeud et al., "Role of CD27/CD70 pathway of activation in immunity and tolerance", Journal of Leukocyte Biology, Feb. 2011, vol. 89, pp. 195-203.

Griffiths et al., "Human anti-self antibodies with high specificity from phage display libraries", The EMBO Journal, 1993, 12:725-734.

Harris et al., "Assessing Genetic Heterogeneity in Production Cell Lines: Detection by Peptide Mapping of a Low Level Tyr to Gln Sequence Variant in a Recombinant Antibody", Biotechnology, 1993, vol. 11, pp. 1293-1297.

International Preliminary Report on Patentability for PCT International Patent Application No. PCT/EP2012/054733, dated Sep. 17, 2013.

International Search Report and Written Opinion for PCT International Patent Application No. PCT/EP2019/085982, dated Mar. 20, 2020.

International Search Report with Written Opinion for PCT International Patent Application No. PCT/EP2017/067923, dated Nov. 15, 2017.

Naresh et al., "Use of the World Health Organization (WHO) classification of non-Hodgkin's lymphoma in Mumbai, India: a review of 200 consecutive cases by a panel of five expert hematopathologists", Leukemia & Lymphoma, Aug. 2004, 45(8):1569-1577.

Sawalha et al., "Defective DNA methylation and CD70 overexpression in CD4+ T cells in MRL/lpr lupus-prone mice", European Journal of Immunology, 2007, vol. 37, pp. 1407-1413.

Ward et al., Binding activities of a repertoire of single immunoglobin variable domains secreted from *Escherichia coli*, Nature, 1989, 341:544-546.

Webster's New World Dictionary, Third College Edition, 1988, see p. 1067 (Year: 1988).

Wei et al., "Midostaurin, enasidenib, CPX-351, gemtuzumab ozogamicin, and venetoclax bring new hope to AML", Blood, Dec. 7, 2017, 130(23): 2469-2474.

Weinberg, "Tumors resemble wound-healing sites", The Biology of Cancer, 2007, Chapter 13.2-13.3, pp. 536-539.

Williams et al. (1996) "Sequence and evolution of the human germline V lambda repertoire," J. Mol. Biol. 264:220-232.

Yanagisawa et al., "Effects of anti-CD70 mAb on Thieler's murine encephalomyelitis virus-induced demyelinating disease", Brain Research, 2010, vol. 1317, pp. 236-245.

Aftimos et al., "Phase I Dose-Escalation Study of the Anti-CD70 Antibody ARGX-110 in Advanced Malignancies", Clinical Cancer Research, Nov. 2017, 23(21):6411-6420.

(56) References Cited

OTHER PUBLICATIONS

International Preliminary Report on Patentability for PCT International Patent Application No. PCT/EP2019/085982, dated Jun. 19, 2020.
Pollyea et al., "Venetoclax with azacitidine disrupts energy metabolism and targets leukemia stem cells in patients with acute myeloid leukemia", Nat Medicine, Nov. 12, 2018, 24(12):1859-1866.
Teh et al., "Enhancing venetoclax activity in acute myeloid leukemia by co-targeting MCL1", Leukemia, Jul. 28, 2017, 32(2): 303-312.
Pan et al., "Selective BCL-2 Inhibition by ABT-199 Causes On-Target Cell Death in Acute Myeloid Leukemia," Cancer Discov. 2014: 363-375.
Achour et al. (2008) "Tetrameric and homodimeric camelid IgGs originate from the same IgH locus," J. Immunol. 181:2001-2009.
Adam et al. 'CD70 (TNFSF7) is Expressed at High Prevalence in Renal Cell Carcinomas and is Rapidly Internalised on Antibody Binding' British J of Cancer; Aug. 7, 2006, vol. 95, No. 3, pp. 298-306.
Appel et al., Molecular Diversity, 1996, 2:29-34.
Askmyr et al. (2013) "Selective killing of candidate AML stem cells by antibody targeting of IL1RAP," Blood, 121 (18):3709-3713.
Baccarani et al. (2006) "Evolving concepts in the management of chronic myeloid leukemia: recommendations from an expert panel on behalf of the European LeukemiaNet," Blood 108:1809-1820.
Belloc et al. (2007) "Imatinib and nilotinib induce apoptosis of chronic myeloid leukemia cells through a Bim-dependant pathway modulated by cytokines," Cancer Biol. Ther. 6:912-919.
Bertrand et al. (2013) "The Costimulatory Molecule CD70 is Regulated by Distinct Molecular Mechanisms and is Associated with Overall Survival in Diffuse Large B-cell Lymphoma," Genes, Chromosomes and Cancer, 52:764-774.
Bosman et al. (2016) "Constitutive NF-KB activation in AML: Causes and treatment strategies," Critical Reviews in Oncology/Hematology, 98:35-44.
Boursalian et al. (2009) "Targeting CD70 for human therapeutic use," Advances in Experimental Medicine and Biology. 647:108-119.
Brown et al. (1996) "Tolerance of single, but not multiple, amino acid replacements in antibody VH CDE 2: a means of minimizing B cell wastage from somatic hypermutation?" J Immunol. 156(9):3285-3291.
Caron et al. (1992) "Engineered Humanized Dimeric Forms of IgG Are More Effective Antibodies," J. Exp. Med., 176:1191-1195.
Chahlavi et al. (2005) "Glioblastomas Induce T-Lymphocyte Death by Two Distinct Pathways Involving Gangliosides and CD70," Cancer Res., 65(12):5428-5438.
Chan et al. (2010) "Therapeutic antibodies for autoimmunity and inflammation," Nature Reviews: Immunology, 10:301-316.
Claus et al. (2012) "CD27 Signaling Increases the Frequency of Regulatory T Cells and Promotes Tumor Growth," Cancer Res., 72(14):3664-3676.
Clevers et al. (2012) "Wnt/β-catenin signaling and disease," Cell. 149:1192-1205.
ClinicalTrials.gov (First received Dec. 16, 2011) "AMG 172 First in Human Study in Patients With Kidney Cancer," U.S. National Institutes of Health. ClinicalTrials.gov Identifier: NCT01497821.
ClinicalTrials.gov (First received Dec. 3, 2013) "A Study of Vantictumab (OMP-18R5) in Combination With Nab-Paclitaxel and Gemcitabine in Previously Untreated Stage IV Pancreatic Cancer," U.S. National Institutes of Health. ClinicalTrials.gov Identifier: NCT02005315.
ClinicalTrials.gov (First received Jul. 17, 2011) "Phase I Clinical Study of CWP232291 in Acute Myeloid Leukemia Patients," U.S. National Institutes of Health. ClinicalTrials.gov Identifier: NCT01398462.
ClinicalTrials.gov (First received May 4, 2011) "A Study of LGK974 in Patients With Malignancies Dependent on Wnt Ligands," U.S. National Institutes of Health. ClinicalTrials.gov Identifier:

NCT01351103. Accessible on the Internet at URL: http://www.ebi.ac.uk/arrayexpress/experiments/E-MEXP-480. [Last Accessed Dec. 15, 2016].
ClinicalTrials.gov (First received Oct. 25, 2013) "A Study of Vantictumab (OMP-18R5) in Combination With Paclitaxel in Locally Recurrent or Metastatic Breast Cancer," U.S. National Institutes of Health. ClinicalTrials.gov Identifier: NCT01973309.
ClinicalTrials.gov (First received Sep. 27, 2013) "A Study of Vantictumab (OMP-18R5) in Combination With Docetaxel in Patients With Previously Treated NSCLC," U.S. National Institutes of Health. ClinicalTrials.gov Identifier: NCT01957007.
Colovai et al. (2007) "Expression of Inhibitory Receptor ILT3 on Neoplastic B Cells Is Associated with Lymphoid Tissue Involvement Leukemia," Cytometry Part B (Clinical Cytometry) 72B:354-362.
Coluccia et al. (2007) "Bcr-Abl stabilizes β-catenin in chronic myeloid leukemia through its tyrosine phosphorylation," EMBO J. 26:1456-1466.
Corbin et al. (2011) "Human chronic myeloid leukemia stem cells are insensitive to imatinib despite inhibition of BCR-ABL activity," J. Clin. Invest. 121:396-409.
Cortes et al. (Nov. 29, 2012) "Ponatinib in refractory Philadelphia chromosome-positive leukemias," N. Engl. J. Med. 367:2075-2088.
Damschroder et al. (2004) "Analysis of human and primate CD2 molecules by protein sequence and epitope mapping with anti-human CD2 antibodies," Mol. Immunol. 41(10):985-1000.
Deininger (2007) "Optimizing therapy of chronic myeloid leukemia," Exp. Hematol. 35:144-154.
Dempke et al. (2017) "Second—and third-generation drugs for immune-oncology treatment—The more the better?," European Journal of Cancer 74(10):55-72.
Deveraux et al. (1984) "A comprehensive set of sequence analysis programs for the VAX," Nucleic Acids Research, 12(1):387-395.
Diegemann et al. (2006) "Immune Escape for Renal Cell Carcinoma: CD70 Mediates Apoptosis in Lymphocytes," Neoplasia, 8(11):933-938.
Dohner et al. (2017) "Diagnosis and management of AML in adults: 2017 ELN recommendations from an international expert panel," Blood, 129(4):66 pages.
Druker et al. (2001) "Activity of a Specific Inhibitor of the BCR-ABL Tyrosine Kinase in the Blast Crisis of Chronic Myeloid Leukemia and Acute Lymphoblastic Leukemia with the Philadelphia Chromosome," N. Engl. J. Med. 344:1038-1042.
Druker et al. (2001) "Efficacy and Safety of a Specific Inhibitor of the BCR-ABL Tyrosine Kinase in Chronic Myeloid Leukemia," N. Engl. J. Med. 344:1031-1037.
Edwards et al. (J. Mol. Biol. (2003) 334, 103-118). (Year: 2003).
EMBL-EBI Database [Online] (Last updated May 3, 2014) "E-MEXP-480—Transcription profiling of D34+ BCR-ABL+ cells of CML patients in chronic phase or blast crisis to identify differentially expressed stage-specific genes," Accession No. E-MEXP-480. Accessible on the Internet at URL: http://www.ebi.ac.uk/arrayexpress/experiments/E-MEXP-480. [Last Accessed Dec. 15, 2016].
Faderl et al. (1999) "The Biology of Chronic Myeloid Leukemia," N. Engl. J. Med. 341:164-172.
Frank, Immunology and Evolution of Infectious Disease, Chapter 4 "Specificity and CrossReactivity," Princeton University Press, 2002.
French et al.: 'Eradication of Lymphoma by CD8 T Cells Following Anti-CD40 Monoclonal Antibody Therapy is Critically Dependent on CD27 Costimulation'. Blood; Jun. 1, 2007, vol. 109, No. 11, pp. 4810-4815.
Genbank Database [Online] (Nov. 2, 2016) "RecName: Full=Proto-oncogene Wnt-1; AltName: Full=Proto-oncogene Int-1 homolog; Flags: Precursor," Accession No. P04628. Accessible on the Internet at URL: https://www.ncbi.nlm.nih.gov/protein/P04628. [Last Accessed Dec. 16, 2016].
Glouchkova et al. (2009) J Immunol 182:718-725.
Goncalves-Silva et al. (2015) "Differential expression and biochemical activity of the immune receptor Tim-3 in healthy and malignant human myeloid cells," Oncotarget, 6(32):33823-33833.
Goto et al. (2012) "Serum soluble CD27 level is associated with outcome in patients with diffuse large B-cell lymphoma treated with

(56) References Cited

OTHER PUBLICATIONS rituximab, cyclophosphamide, doxorubicin, vincristine and prednisolone," Leukemia and Lymphoma, 53(8):1494-1500.
Gregory et al., Cancer Cell, 2010, 18:74-87.
Groves et al. (2006) "Affinity maturation of phage display antibody populations using ribosome display," Journal of Immunological Methods. 313:129-139.
Hamad et al. (Hindawi Publishing Corporation, Stem Cells International, 2013, 12 pages).
Han et al. (2005) "Increased prevalence of activated CD70+ CD4+ T cells in the periphery of patients with systematic lupus erythematosus," Lupus 14:598-606.
Hanekamp et al. (2017) "Leukemic stem cells: identification and clinical application," Int. J. Hematol., 105:549-557.
Harlow et al. (1988) Antibodies, A Laboratory Manual. Cold Spring Harbor laboratory, pp. 37-47.
Held-Feindt et al. (2002) "CD70/CD27 Ligand, a member or the TNF family, is expressed in human brain tumors," Int. J. Cancer, 98:352-356.
Hinton et al. (2006) "An Engineered Human IgG 1 Antibody with Longer Serum Half-Life," The Journal of Immunology, 176:346-356.
Hishima et al. (2000) "CD70 Expression in Thymic Carcinoma," The American Journal of Surgical Pathology, 2:742-746.
Holliger et al. (2005) "Engineered antibody fragments and the rise of single domains," Nature Biotechnology, 23(9):1126-1136.
Hsiao et al. (2008) "Tankyrase function at telomeres, spindle poles, and beyond," Biochimie. 90:83-92.
Hu et al., Leukemia, 2009, 23:109-116.
International Preliminary Report on Patentability, PCT/EP2012/054733, dated Sep. 17, 2013, 12 pages.
International Search Report and Written Opinion corresponding to International Patent Application No. PCT/EP2018/066144, dated Aug. 17, 2018.
International Search Report and Written Opinion for International Application No. PCT/EP2019/051058, dated Mar. 21, 2019.
International Search Report, PCT/EP2012/054733, dated Jul. 26, 2012, 5 pages.
Israel et al. (2005) "Anti-CD70 antibodies: a potential treatment for EBV+ CD70-expressing lymphomas," Mol. Cancer Ther. 4:2037-2044.
Jacobs et al. (2015) "CD70: An emerging target in cancer immunotherapy," Pharmacology and Therapeutics 155:1-10.
Jacobs et al. (2015) "Unlocking the potential of CD70 as a novel immunotherapeutic target for non-small cell lung cancer," Oncotarget, 6(15):13462-13475.
Jak et al. (Leukemia & Lymphoma, May 2009; 50(5): 788-801) (Year: 2009).
Jan et al. (2011) "Prospective separation of normal and leukemic stem cells based on differential expression of TIM3, a human acute myeloid leukemia stem cell marker," PNAS, 108(12):5009-5014.
Japp et al. (2015) "Dysfunction of PSA-specific CD8+ cells in prostate cancer patients correlates with CD38 and Tim-3 expression," Cancer of Immunol Immunother, 8 pages.
Jaras et al. (2010) "Isolation and killing of candidate chronic myeloid leukemia stem cells by antibody targeting of IL-1 receptor accessory protein," PNAS, 107(37):16280-16285.
Jilaveanu et al. (2012) "CD70 Expression Patterns in Renal Cell Carcinoma," Human Pathol., 43(9):1394-1399.
Junker et al. (2005) "CD70: A new tumor specific biomarker for renal cell carcinoma," 173:2150-2153.
Kang et al. (2015) "The ITM-containing receptor LAIR1 is essential for acute myeloid leukemia development," Nat. Cell Biol., 17(5):665-677.
Kapinas et al. (2010) "miR-29 modulates Wnt signaling in human osteoblasts through a positive feedback loop," J. Biol. Chem. 285:25221-25231.
Katoh et al. (2007) "WNT signaling pathway and stem cell signaling network," Clin. Cancer Res. 13(14):4042-4045.
Kavalerchik et al. (2008) "Chronic myeloid leukemia stem cells," J. Clin. Oncol. 26:2911-2915.
Kikushige et al. (2010) "TIM-3 is a promising target to selectively kill acute myeloid leukemia stem cells," Cell Stem Cell, 7:708-717.
Kikushige et al. (2013) "TIM-3 as a novel therapeutic target for eradicating acute myelogenous leukemia stem cells," Int. J. Hematol., 98:627-633.
Kikushige et al. (2015) "A TIM-3/Gal-9 Autocrine Stimulatory Loop Drives Self-Renewal of Human Myeloid Leukemia Stem Cells and Leukemic Progression," Cell Stem Cell, 17:341-352.
Koren-Michowitz et al. (Jan. 12, 2012) "Imatinib plasma trough levels in chronic myeloid leukaemia: results of a multicentre study CSTI571AIL11TGLIVEC," Hematol. Oncol. 30:200-205.
Lee et al. (2007) "Unchecked CD70 expression on T cells lowers threshold for T-cell activation in rheumatoid arthritis," J. Immunol., 179(4):2609-2615.
Lens et al. (1999) "Aberrant expression and reverse signaling of CD70 on malignant B cells," British Journal of Hematology, 106:491-503.
Li et al. (Feb. 14, 2012) "Activation of p53 by SIRT1 inhibition enhances elimination of CML leukemia stem cells in combination with imatinib," Cancer Cell. 21:266-281.
Liu et al. (2010) "Sp1/NFKB/HDAC/miR-29b Regulatory Network in KIT-driven Myeloid Leukemia," Cancer Cell. 17:333-347.
Lloyd et al., Protein Engineering, Design & Selection vol. 22 No. 3 pp. 159-168 (2009).
Lugo et al. (1990) "Tyrosine kinase activity and transformation potency of bcr-abl oncogene products," Science. 247:1079-1082.
McEarchern et al. (2008) "Preclinical Characterization of SGN-70, a Humanized Antibody Directed Against CD70," Clin. Cancer Res. 14(23):7763-7772.
McKinney, J Neural Neurosurg Psychiatry 2004;75(Suppl II):ii12-ii17 (2004).
Memorandum, Feb. 22, 2018, Robert W. Bahr, Deputy Commissioner for Patent Examination Policy, pp. 1-2 (2018).
Meyer et al., British Journal of Haematology, 2018, 180, 808-820 (2018).
Naresh et al., Leukemia & Lymphoma, Aug. 2004 Vol. 45 (8), pp. 1569-1577 (2004).
Natsume et al. (2009) "Improving effector functions of antibodies for cancer treatment: Enhancing ADCC and CDC," Drug Design Development and Therapy, 3:7-16.
Nilsson et al. (2005) "Expression of CD27-CD70 on Early B Cell Progenitors in the Bone Marrow: Implication and Therapy of Childhood ALL," Experimental Hematology, 33:1500-1507.
Nolte et al., Immunological Reviews 2009, vol. 2009: 2016-231.
O'Donnell et al. (2017) "Acute Myeloid Leukemia, Version 3," Journal of the National Comprehensive Cancer Network, 15(7):926-957.
O'Hare et al. (2009) "AP24534, a Pan-BCR-ABL Inhibitor for Chronic Myeloid Leukemia, Potently Inhibits the T315I Mutant and Overcomes Mutation-Based Resistance," Cancer Cell. 16:401-412.
Oelke et al. (2004) "Overexpression of CD70 and Overstimulation of IgG Synthesis by Lupus T Cells and T Cells Treated with DNA Methylation Inhibitors," Arthritis and Rheumatism, 50(6):1850-1860.
Ohaegbulam et al. (2015) "Human cancer immunotherapy with antibodies to the PD-1 and PD-L1 pathway," Trends Mol. Med., 21(1):24-33.
O'Hare et al., Nature Reviews Cancer, 2012, 12:513-526.
Padlan (1994) "Anatomy of the antibody molecule," Mol. Immunol. 31(3):169-217.
Perna et al. (2017) "Integration Proteomics and Transcriptomics for Systematic Combinatorial Chimeric Antigen Receptor Therapy of AML," Cancer Cell, 32:506-519.
Petrau et al. (2014) "CD70: A potential target in breast cancer?," Journal of Cancer, 5:761-764.
Polakis (2012) "Drugging Wnt signalling in cancer," EMBO J. 31(12):2737-2746.
Pollyea et al. (2017) "Therapeutic targeting of acute myeloid leukemia stem cells," Blood, 129(12):1627-1635.

(56) References Cited

OTHER PUBLICATIONS

Ponce et al. (2017) "SIRPa-antibody fusion proteins stimulate phagocytosis and promote elimination of acute myeloid leukemia cells," Oncotarget, 8(7):11284-11301.
Portolano et al. (1993) "Lack of promiscuity in autoantigen-specific H and L chain combinations as revealed by human H and L chain 'roulette,'" J. Immunol. 150(3):880-887.
Presta et al. (2008) "Molecular engineering and design of therapeutic antibodies," Current Opinion in Immunology, 20:460-470.
Ragusa et al., BMC Cancer 2010, 10: 377.
Ranheim et al., Blood. 1995, pp. 3556-3565 (1995).
Richardson et al. (2014) "Epigenetics in 2013: DNA methylation and miRNA- key roles in systematic autoimmunity," Nat. Rev. Rheumatol., 10(2):72-74.
Riether et al. (2017) "CD70/CD27 signaling promotes blast stemness and is a viable therapeutic target in acute myeloid leukemia," J. Exp. Med., 214(2):359-380.
Ring et al. (2017) "Anti-SIRPa antibody immunotherapy enhances neutrophil and macrophage antitumor activity," PNAS, 114(49):E10578-E10585.
Rudikoff et al. (1982) "Single amino acid substitution altering antigen-binding specificity," Proc. Natl. Acad. Sci. USA. 79:1979-1983.
Ryan et al. (2010) "Targeting pancreatic and ovarian carcinomas using the auristatin-based anti-CD70 antibody-drug conjugate SGN-75," British Journal of Cancer. 103:676-684.
Sakuishi et al. (2010) "Targeting Tim-3 and PD-1 pathways to reverse T cell exhaustion and restore anti-tumor immunity," J. Exp. Med., 207(10):2187-2194.
Schürch et al. (Feb. 1, 2012) "CD27 signaling on chronic myelogenous leukemia stem cells activates Wnt target genes and promotes disease progression," J. Clin. Invest. 122:624-638.
Shao et al. (2011) "Combination or monoclonal antibodies with DST inhibits accelerated rejection mediated by memory T cells to induce long-lived heart allograft acceptance in mice," Immunology Letters 138:122-128.
Shopes et al. (1992) "A genetically engineered human IgG mutant with enhanced cytolytic activity," The Journal of Immunology, 148:2918-2922.
Shultz et al. (2005) "Human Lymphoid and Myeloid Cell Development in NOD/LtSz-scid IL2Rynull Mice Engrafted with Mobilized Human Hemopoietic Stem Cells," J. Immunol. 174:6477-6489.
Silence et al. (2014) "ARGX-110, a highly potent antibody targeting CD70, eliminates tumors via both enhanced ADCC and immune checkpoint blockade," mAbs, 6(2):523-532.
Sloan et al. (2004) "Detection of Differentially Expressed Genes in an Isogenic Breast Metastasis Model using RNA Arbitrarily Primed-Polymerase Chain Reaction Coupled with Array Hybridization (RAP-Array)," American Journal of Pathology, 164(1):315-323.
Tan et al. (Aug. 9, 2013) "Suppression of Wnt Signaling by the miR-29 Family Is Mediated by Demethylation of WIF-1 in Non-Small-Cell Lung Cancer," Biochem. Biophys. Res. Commun. 438:673-679.
Tesselaar et al. (1997) "Characterization of murine CD70, the ligand of the TNF receptor family member CD27," J. Immunol. 159:4959-4965.
Tesselaar et al. (2003) "Expression of the murine CD27 ligand CD70 in vitro and in vivo," J. Immunol. 170:33-40.
Theocharides et al. (2012) "Disruption of SIRPa signaling in macrophages eliminates human acute myeloid leukemia stem cells in xenografts," J. Exp. Med., 209(10):1883-1899.
Uniprot Database [Online] (Feb. 6, 2007) "UniProtKB-A1Z199 (A1Z199_HUMAN)," Accession No. A1Z199. Accessible on the Internet at URL: http://www.uniprot.org/uniprot/A1Z199. [Last Accessed Dec. 16, 2016].
Uniprot Database [Online] (Nov. 1, 1996) "UniProtKB-Q13745 (Q13745_HUMAN)," Accession No. Q13745. Accessible on the Internet at URL: http://www.uniprot.org/uniprot/Q13745. [Last Accessed Dec. 16, 2016].

Vaccaro et al. (2005) "Engineering the FC region of immunoglobulin G to modulate in vivo antibody levels," Nature Biotechnology, 23(10):1283-1288.
Vajdos et al. (2002) "Comprehensive Functional Maps of the Antigen-binding Site of an Anti-ErbB2 Antibody Obtained with Shotgun Scanning Mutagenesis," J. Mol. Biol. 320(2):415-428.
Van Doorn et al. (2004) "Aberrant Expression of the Tyrosine Kinase Receptor EphA4 and the Transcription Factor Twist in Sezary Syndrome Identified by Gene Expression Analysis," Cancer Research, 64:5578-5586.
Van Regenmortel, Journal of Immunological Methods, 1998, 216:37-48.
Voronkov et al. (2013) "Wnt/beta-catenin signaling and small molecule inhibitors," Current Pharmaceutical Design. 19:634-664.
Waaler et al. (2012) "A novel tankyrase inhibitor decreases canonical Wnt signaling in colon carcinoma cells and reduces tumor growth in conditional APC mutant mice," Cancer Res. 72(11):2822-2832.
Wajant, H. (2006) "Therapeutic targeting of CD70 and CD27," Expert Opinion on Therapeutic Targets, 20(8):959-973.
Wang et al. (2007) "Antibody Structure, Instability, and Formulation," Journal of Pharmaceutical Sciences, 96(1):1-26.
Wang et al. (2012) "Distinctive Features of the Differentiated Phenotype and Infiltration of Tumor-reactive Lymphocytes in Clear Cell Renal Cell Carcinoma," Cancer Res., 72(23):6119-6129.
WANG et al. (2017) "Circular RNAs in human cancer," Molecular Cancer, 16(25):8 pages.
Webster's New World Dictionary, Third College Edition, 1988, see p. 1067 (1988).
Wischhusen et al. (2002) "Identification of CD70-mediated Apoptosis of Immune Effector Cells as a Novel Immune Escape Pathway of Human Glioblastoma," Cancer Research, 62:2592-2599.
Yamane-Ohnuke et al. (2009) "Production of therapeutic antibodies with controlled fucosylation," mAbs, 1(3):230-236.
Yang et al. (2014) "TGF-β upregulates CD70 expression and induces exhaustion of effector memory T cells in B-cell non-Hodgkin's lymphoma," Leukemia, 28(9):1872-1884.
Yeung et al. (2009) "Engineering Human lgG1 Affinity to Human Neonatal Fc Receptor: Impact of Affinity Improvement on Pharmacokinetics in Primates," The Journal of Immunology, 182:7663-7671.
Zahnd et al. (2010) "Computational analysis of off-rate selection experiments to optimize affinity maturation by directed evolution," Protein Engineering: Design & Selection. 23(4):175-184.
Zalevsky et al. (2010) "Enhanced antibody half-life improves in vivo activity," Nat. Biotechnol., 28(2):157-159.
Zhang et al. (2010) "Effective targeting of quiescent chronic myelogenous leukemia stem cells by histone deacetylase inhibitors in combination with imatinib mesylate," Cancer Cell. 17:427-442.
Zhou et al. (2011) "Histone modifications and methyl-CpG-binding domain protein levels at the TNFSF7 (CD70) promoter in SLE CD4+ T cells," Lupus, 20:1365-1371.
U.S. Appl. No. 14/005,113, filed Jan. 24, 2014, 2014/0141016, May 22, 2014, U.S. Pat. No. 9,765,148, Sep. 19, 2017, Karen Silence.
U.S. Appl. No. 14/073,462, filed Nov. 6, 2016, 2014/0147450, May 29, 2014, U.S. Pat. No. 8,834,882, Sep. 16, 2014, Karen Silence.
U.S. Appl. No. 14/163,752, filed Jan. 24, 2014, 2014/0235843, Aug. 21, 2014, U.S. Pat. No. 9,765,149, Sep. 19, 2017, Karen Silence.
U.S. Appl. No. 14/626,038, filed Feb. 19, 2015, 2015/0266963, Sep. 24, 2015, U.S. Pat. No. 11,072,665, Jul. 27, 2021, Karen Silence.
U.S. Appl. No. 16/278,522, filed Feb. 18, 2019, 2019/0270823, Sep. 5, 2019, Karen Silence.
U.S. Appl. No. 14/832,333, filed Aug. 21, 2015, U.S. Pat. No. 10,391,168, Aug. 27, 2019, Carsten Riether.
U.S. Appl. No. 16/506,546, filed Jul. 9, 2019, Carsten Riether.
U.S. Appl. No. 16/011,342, filed Jun. 18, 2018, 2019/0106498, Apr. 11, 2019, Hans de Haard.
U.S. Appl. No. 16/249,480, filed Jan. 16, 2019, 2019/0241668, Aug. 8, 2019, Luc Van Rompaey.

* cited by examiner

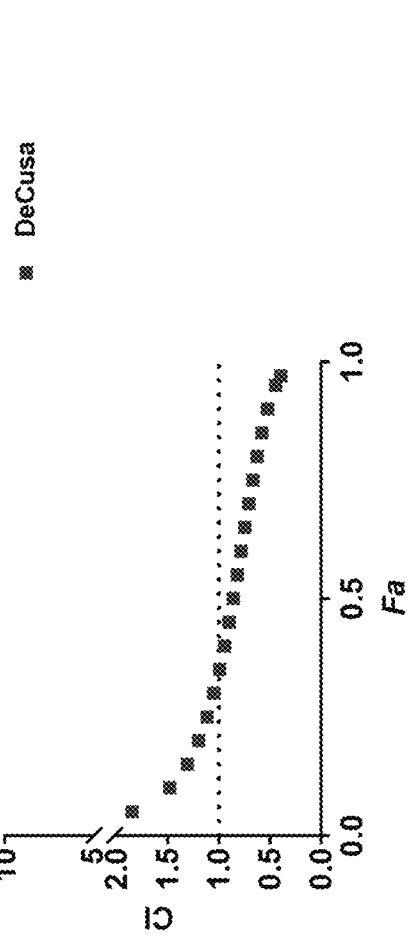
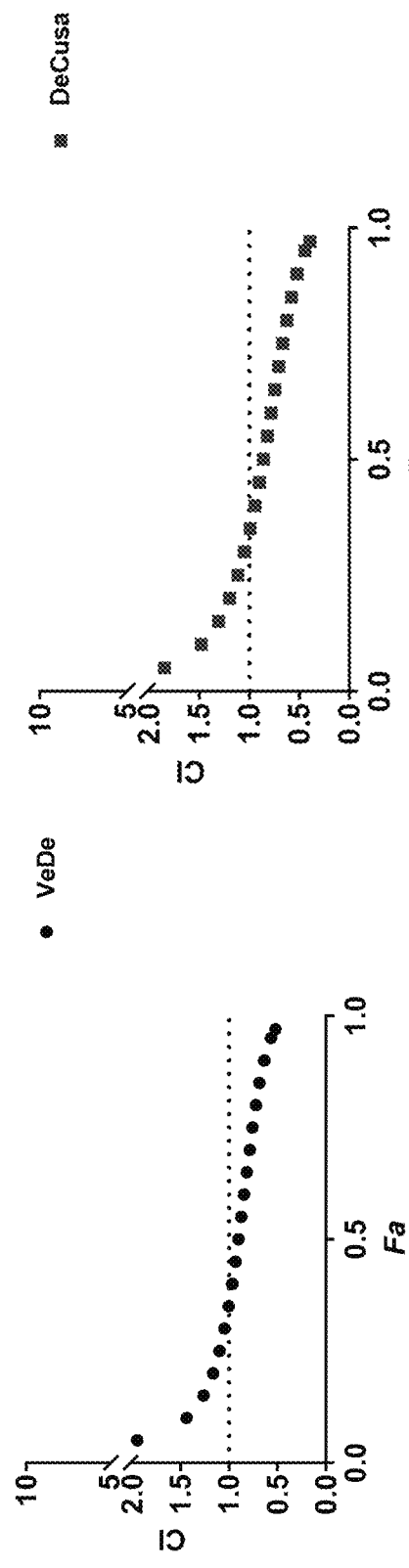
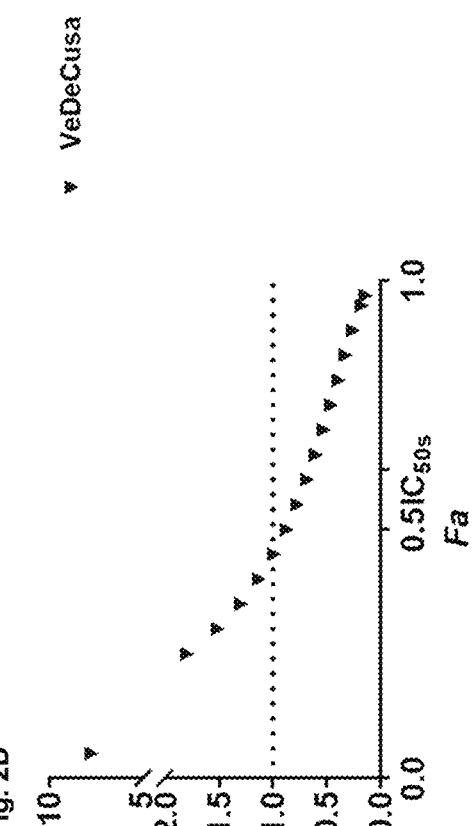
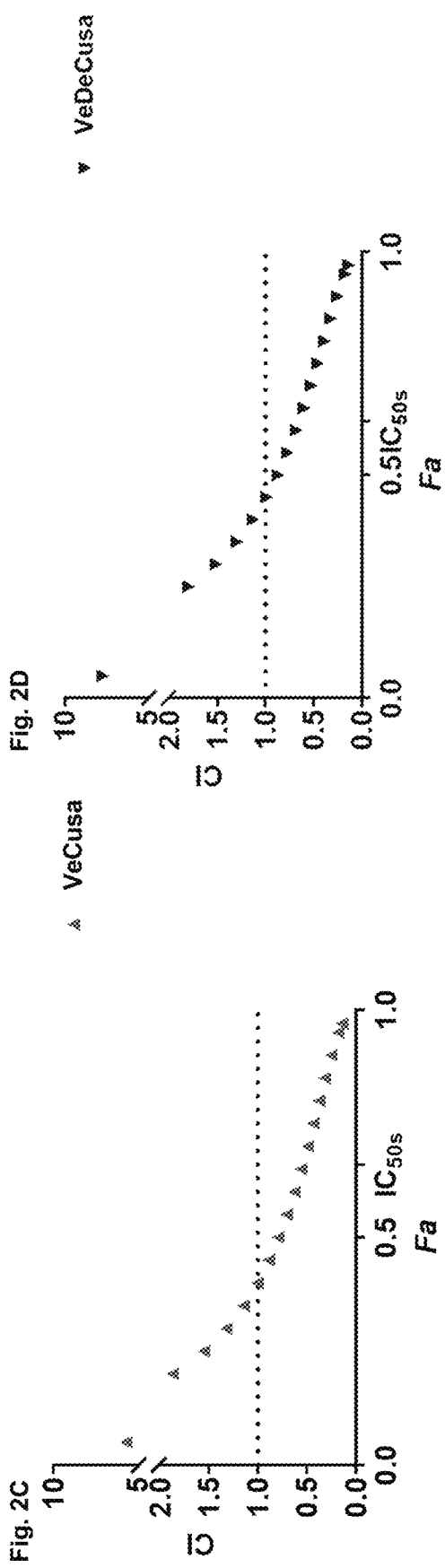

NB4 cells
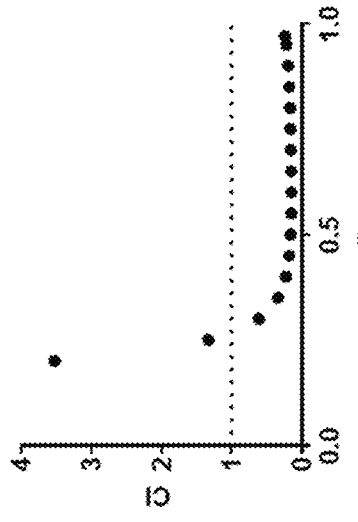
Fig. 3A VeDe
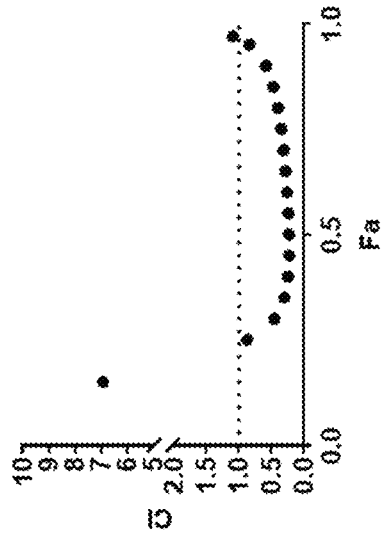
Fig. 3B VeCusa
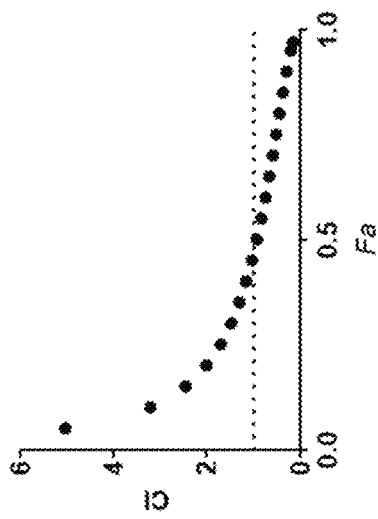
Fig. 3C DeCusa
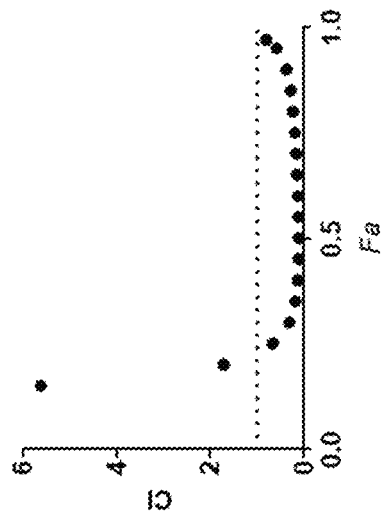
Fig. 3D VeDeCusa MOLM-13 cells Fig. 7A  1st plating
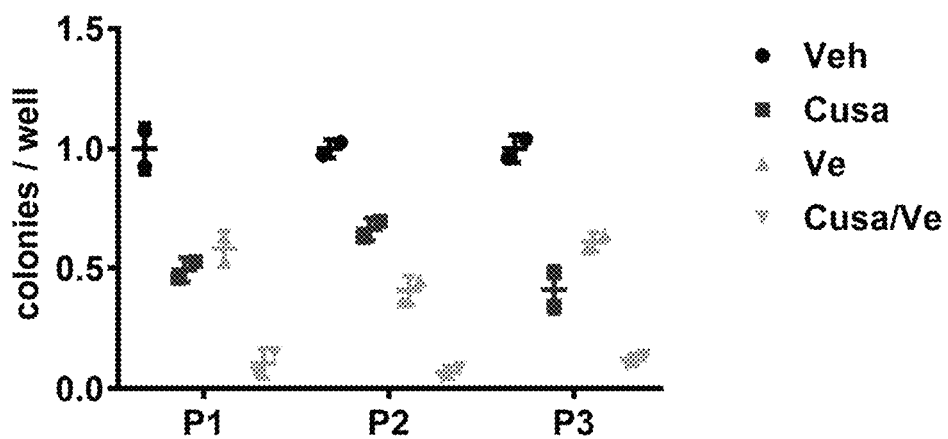
Fig. 7B  2nd plating
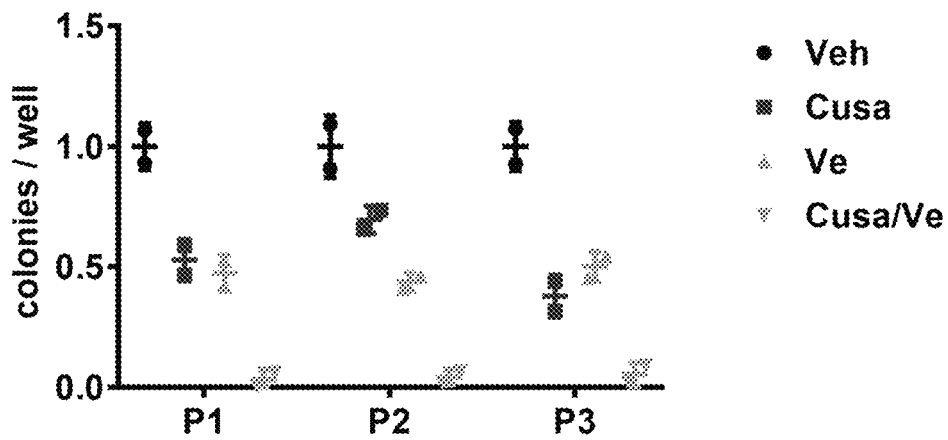

CD70 COMBINATION THERAPY

RELATED APPLICATIONS

This application claims the benefit of priority of Great Britain Patent Application Nos. 1820582.3, filed Dec. 18, 2018; 1911007.1, filed Aug. 1, 2019; and 1917701.3, filed Dec. 4, 2019, the disclosures of which are hereby incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 18, 2019, is named 617571_AGX5-049_ST25.txt and is 3,787 bytes in size.

FIELD OF THE INVENTION

The present invention relates to combination therapies, particularly combination therapies for the treatment of myeloid malignancy. The combination therapies are particularly useful for the treatment of acute myeloid leukemia (AML). The combination therapies include an antibody or antigen binding fragment thereof that binds to CD70 and a BCL-2 inhibitor, for example venetoclax or a pharmaceutically acceptable salt thereof. The combination therapies may further include an additional anti-cancer agent, for example an agent used for the treatment of AML such as azacitidine or decitabine.

BACKGROUND TO THE INVENTION

In recent years, the development of new cancer treatments has focussed on molecular targets, particularly proteins, implicated in cancer progression. The list of molecular targets involved in tumour growth, invasion and metastasis continues to expand, and includes proteins overexpressed by tumour cells as well as targets associated with systems supporting tumour growth such as the vasculature and immune system. The number of therapeutic or anti-cancer agents designed to interact with these molecular targets also continues to increase. A large number of targeted cancer medicines are now approved for clinical use with many more in the developmental pipeline.

CD70 has been identified as a molecular target of particular interest owing to its constitutive expression on many types of hematological malignancies and solid carcinomas (Junker et al. (2005) *J Urol.* 173:2150-3; Sloan et al. (2004) *Am J Pathol.* 164:315-23; Held-Feindt and Mentlein (2002) *Int J Cancer* 98:352-6; Hishima et al. (2000) *Am J Surg Pathol.* 24:742-6; Lens et al. (1999) Br J Haematol. 106: 491-503; Boursalian et al. (2009) *Adv Exp Med Biol.* 647: 108-119; Wajant H. (2016) *Expert Opin Ther Targets* 20(8): 959-973). CD70 is a type II transmembrane glycoprotein belonging to the tumour necrosis factor (TNF) superfamily, which mediates its effects through binding to its cognate cell surface receptor, CD27. Both CD70 and CD27 are expressed by multiple cell types of the immune system and the CD70-CD27 signalling pathway has been implicated in the regulation of several different aspects of the immune response. This is reflected in the fact that CD70 overexpression occurs in various auto-immune diseases including rheumatoid and psoriatic arthritis and lupus (Boursalian et al. (2009) *Adv Exp Med Biol.* 647:108-119; Han et al. (2005) *Lupus* 14(8):598-606; Lee et al. (2007) *J Immunol.* 179(4): 2609-2615; Oelke et al. (2004) *Arthritis Rheum.* 50(6):1850-1860).

CD70 expression has been linked to poor prognosis for several cancers including B cell lymphoma, renal cell carcinoma and breast cancer (Bertrand et al. (2013) *Genes Chromosomes Cancer* 52(8):764-774; Jilaveanu et al. (2012) *Hum Pathol.* 43(9):1394-1399; Petrau et al. (2014) *J Cancer* 5(9):761-764). CD70 expression has also been found on metastatic tissue in a high percentage of cases indicating a key role for this molecule in cancer progression (Jacobs et al. (2015) *Oncotarget* 6(15):13462-13475). Constitutive expression of CD70 and its receptor CD27 on tumour cells of hematopoietic lineage has been linked to a role of the CD70-CD27 signalling axis in directly regulating tumour cell proliferation and survival (Goto et al. (2012) *Leuk Lymphoma* 53(8):1494-1500; Lens et al. (1999) *Br J Haematol.* 106(2); 491-503; Nilsson et al. (2005) *Exp Hematol.* 33(12):1500-1507; van Doorn et al (2004) *Cancer Res.* 64(16):5578-5586).

Upregulated CD70 expression on tumours, particularly solid tumours that do not co-express CD27, also contributes to immunosuppression in the tumour microenvironment in a variety of ways. For example, CD70 binding to CD27 on regulatory T cells has been shown to augment the frequency of Tregs, reduce tumour-specific T cells responses and promote tumour growth in mice (Claus et al. (2012) *Cancer Res.* 72(14):3664-3676). CD70-CD27 signalling can also dampen the immune response by tumour-induced apoptosis of T-lymphocytes, as demonstrated in renal cell carcinoma, glioma and glioblastoma cells (Chahlavi et al. (2005) *Cancer Res.* 65(12):5428-5438; Diegmann et al. (2006) *Neoplasia* 8(11):933-938; Wischusen et al. (2002) *Cancer Res* 62(9):2592-2599). Finally, CD70 expression has also been linked to T cell exhaustion whereby the lymphocytes adopt a more differentiated phenotype and fail to kill the tumour cells (Wang et al. (2012) *Cancer Res* 72(23):6119-6129; Yang et al. (2014) *Leukemia* 28(9):1872-1884).

Given the importance of CD70 in cancer development, CD70 is an attractive target for anti-cancer therapy and antibodies targeting this cell surface protein are in clinical development (Jacob et al. (2015) *Pharmacol Ther.* 155:1-10; Silence et al. (2014) *mAbs* 6(2):523-532).

SUMMARY OF INVENTION

The present invention is directed to combination therapies comprising antibodies or antigen binding fragments thereof that bind to CD70. As noted above, the list of proteins implicated in tumour growth continues to expand, and combination therapies that target two or more of these proteins are becoming increasingly attractive as anti-cancer treatments. In the combination therapies of the invention, an antibody or antigen binding fragment thereof that binds to CD70 is combined with a BCL-2 inhibitor, for example venetoclax or a pharmaceutically acceptable salt thereof. Overexpression of BCL-2 in cancer cells confers resistance to apoptosis and therefore inhibition of this protein can promote tumour cell death. As explained elsewhere herein, venetoclax is an example of a potent, selective small-molecule inhibitor of the BCL-2 protein. As reported herein, the combination of an antibody or antigen binding fragment thereof that binds to CD70 and a BCL-2 inhibitor, for example venetoclax or a pharmaceutically acceptable salt thereof, provides an effective therapy for the treatment of cancer, particularly myeloid malignancies such as acute myeloid leukemia (AML).

In a first aspect, the present invention provides a combination comprising (i) an antibody or antigen binding fragment thereof that binds to CD70; and (ii) a BCL-2 inhibitor. In certain preferred embodiments, the BCL-2 inhibitor is Compound (I) as shown below or a pharmaceutically acceptable salt thereof.

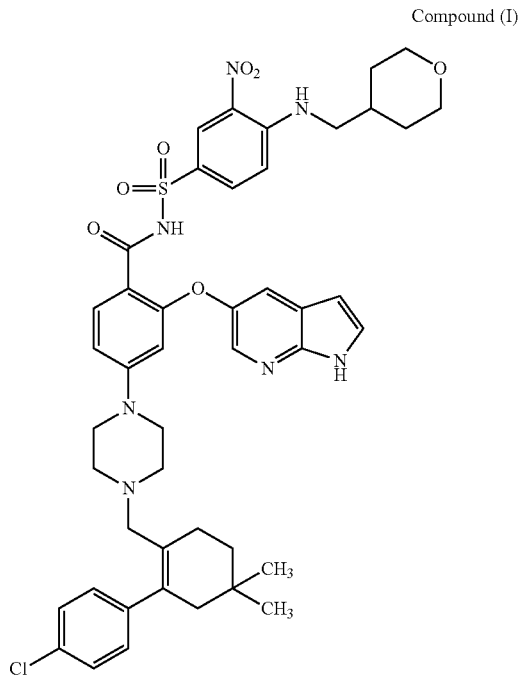 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

Compound (I)

Compound (I) is also referred to herein as venetoclax.

In certain embodiments, the antibody or antigen binding fragment that binds to CD70 is selected from: (i) an antibody or antigen binding fragment comprising a variable heavy chain domain (VH) and a variable light chain domain (VL) comprising the heavy chain CDRs (HCDR3, HCDR2 and HCDR1) and light chain CDRs (LCDR3, LCDR2 and LCDR1): HCDR3 comprising or consisting of SEQ ID NO: 3; HCDR2 comprising or consisting of SEQ ID NO: 2; HCDR1 comprising or consisting of SEQ ID NO: 1; LCDR3 comprising or consisting of SEQ ID NO: 7; LCDR2 comprising or consisting of SEQ ID NO: 6; and LCDR1 comprising or consisting of SEQ ID NO: 5; (ii) an antibody or antigen binding fragment comprising a VH domain comprising an amino acid sequence at least 70%, at least 80%, at least 90%, at least 95% identical to SEQ ID NO:4 and a VL domain comprising an amino acid sequence at least 70%, at least 80%, at least 90%, at least 95% identical to SEQ ID NO:8; or (iii) ARGX-110. In certain embodiments, the antibody is an IgG, preferably an IgG1.

The CD70 antibody or antigen binding fragment of the combinations may possess one or more effector functions. In certain embodiments, the antibody or antigen binding fragment has ADCC activity; and/or comprises a defucosylated antibody domain; and/or has CDC activity; and/or has ADCP activity. In preferred embodiments, the CD70 antibody is ARGX-110.

In certain embodiments, the CD70 antigen binding fragment of the combinations is independently selected from the group consisting of: an antibody light chain variable domain (VL); an antibody heavy chain variable domain (VH); a single chain antibody (scFv); a F(ab')2 fragment; a Fab fragment; an Fd fragment; an Fv fragment; a one-armed (monovalent) antibody; diabodies, triabodies, tetrabodies or any antigen-binding molecule formed by combination, assembly or conjugation of such antigen binding fragments.

In certain embodiments, the CD70 antibody or antigen binding fragment thereof and the BCL-2 inhibitor are formulated as separate compositions. In certain embodiments, the CD70 antibody or antigen binding fragment thereof and venetoclax or a pharmaceutically acceptable salt thereof are formulated as separate compositions.

The combinations of the invention may comprise one or more additional therapeutic agents, for example at least one additional anti-cancer agent, preferably an agent for the treatment of a myeloid malignancy. In certain embodiments, the additional anti-cancer agent is an agent for the treatment of acute myeloid leukemia (AML). In preferred embodiments, the combinations comprise a hypomethylating agent, preferably azacitidine or decitabine.

In a further aspect, the present invention provides combinations according to the first aspect of the invention for use in therapy. In particular, the present invention provides combinations according to the first aspect of the invention for use in the treatment of a malignancy, preferably a myeloid malignancy, in a human subject. The present invention also provides a method for treating a malignancy, preferably a myeloid malignancy, in a human subject, said method comprising administering to the subject an effective amount of any of the combinations according to the first aspect of the invention.

The present invention also provides an antibody or antigen binding fragment thereof that binds to CD70 for use in the treatment of a malignancy, preferably a myeloid malignancy, in a human subject, wherein the antibody molecule is administered in combination with a BCL-2 inhibitor, preferably compound (I) or a pharmaceutically acceptable salt thereof. The present invention also provides a BCL-2 inhibitor, preferably compound (I) or a pharmaceutically acceptable salt thereof, for use in the treatment of a myeloid malignancy in a human subject, wherein the BCL-2 inhibitor, preferably compound (I) or the pharmaceutically acceptable salt thereof, is administered in combination with an antibody or antigen binding fragment thereof that binds to CD70.

The combinations of the invention are particularly advantageous because they exhibit synergistic efficacy. Preferably, therefore, in embodiments of all aspects of the invention, the dose at which the CD70 antibody or antigen binding fragment thereof is administered and/or provided in the combination, and the dose at which the BCL-2 inhibitor is administered and/or provided in the combination, are each selected such that the combination provides synergistic treatment.

In certain preferred embodiments of the combination of the invention, the CD70 antibody or antigen binding fragment thereof and the BCL-2 inhibitor are each present in the combination in an amount sufficient to provide synergistic cell killing when cultured with an AML cell line selected from: NOMO-1, MOLM-13, NB4 and MV4-11.

Regarding the malignancies to be treated using combinations of the invention, said malignancies may be newly-diagnosed myeloid malignancies; relapsed or refractory myeloid malignancies; or myeloid malignancies selected from: acute myeloid leukemia (AML); myelodysplastic syndromes (MDS); myeloproliferative neoplasms (MPN); chronic myeloid leukemia (CML); and chronic myelomonocytic leukemia (CMML). In particularly preferred embodiment, the combinations of the invention are for the treatment of acute myeloid leukemia (AML).

In certain embodiments, the subject or patient treated in accordance with the methods of the invention is a newly-diagnosed AML patient who is ineligible for standard intensive chemotherapy. The subject may be a newly-diagnosed AML patient aged 75 years or older or a newly-diagnosed AML patient having a comorbidity that precludes use of standard intensive chemotherapy.

In certain embodiments, the CD70 antibody or antigen binding fragment thereof is administered at a dose in the range of 0.1-25 mg/kg, preferably 10 mg/kg. Alternatively or in addition, the BCL-2 inhibitor, preferably venetoclax or pharmaceutically acceptable salt thereof, may be administered in a dose in the range 100 mg-600 mg. In preferred embodiments, the methods described herein comprise administering a combination additionally comprising azacitidine wherein the azacitidine is administered at a dose of 75 mg/m$^2$. In further preferred embodiments, the methods described herein comprise administering a combination additionally comprising decitabine wherein the decitabine is administered at a dose of 20 mg/m$^2$.

In certain embodiments, the methods further comprise monitoring of the patient's blast count. The patient's peripheral blood and/or bone marrow blast count may be reduced, for example reduced to less than 25%, for example reduced to 5%, for example reduced to less than 5%, for example reduced to minimal residual disease levels, for example reduced to undetectable levels. In certain embodiments, the bone marrow blast count is reduced to between 5% and 25% and the bone marrow blast percentage is reduced by more than 50% as compared to pretreatment.

In certain embodiments, the methods induce a partial response. In certain embodiments, the methods induce a complete response, optionally with platelet recovery and/or neutrophil recovery. The methods may induce transfusion independence of red blood cells or platelets, or both, for 8 weeks or longer, 10 weeks or longer, 12 weeks or longer. In certain embodiments, the methods reduce the mortality rate after a 30-day period or after a 60-day period.

In certain embodiments, the methods increase survival. For example, the methods may increase survival relative to the standard of care agent or agents used to treat the particular myeloid malignancy being treated with the combination. The methods may induce a minimal residual disease status that is negative.

In certain embodiments, the methods further comprise a step of subjecting the subject to a bone marrow transplantation. Alternatively or in addition, the methods may further comprise a step of administering one or more additional anti-cancer agents. The one or more additional cancer agents may be selected from any agents suitable for the treatment of myeloid malignancies, preferably AML. Preferred agents may be selected from selectin inhibitors (e.g. GMI-1271); FMS-like tyrosine kinase receptor 3 (FLT3) inhibitors (e.g. midostaurin); cyclin-dependent kinase inhibitors; aminopeptidase inhibitors; JAK/STAT inhibitors; cytarabine; anthracycline compounds (e.g. daunorubicin, idarubicin); doxorubicin; hydroxyurea; Vyxeos; IDH1 or IDH2 inhibitors such as Idhifa (or Enasidenib) or Tibsovo (or ivosidenib); Smoothened inhibitors such as Glasdegib, BET bromodomain inhibitors, CD123 or CD33 targeting agents, HDAC inhibitors, LSC targeting agents, AML bone marrow niche targeting agents, and NEDD8-activating enzyme inhibitors such as Pevonedistat.

BRIEF DESCRIPTION OF THE DRAWINGS

FIGS. 2A-2D: Cusatuzumab and decitabine co-treatment synergistically eliminates NOMO-1 AML cells. Individual CI-Fa plots of the data for each combination presented in FIG. 1. (FIG. 2A) venetoclax and decitabine; (FIG. 2B) decitabine and cusatuzumab; (FIG. 2C) venetoclax and cusatuzumab; (FIG. 2D) venetoclax, decitabine and cusatuzumab.

FIGS. 3A-3D: Cusatuzumab and decitabine co-treatment synergistically eliminates NB4 AML cells. NB4 AML cells were treated with vehicle, cusatuzumab, venetoclax or decitabine alone or in combination in a constant ratio in the presence of CFSE-labeled NK cells (ratio 1:1). NB4 AML cell numbers per well were counted after 72 hours, the degree of viable cells was determined by Annexin V staining, and the effect of drug treatment was calculated as the ratio of surviving cells to vehicle-treated cells. Combination index (CI) values were calculated, and values between 0 and 10 were plotted against fraction affected (Fa) values. Fa-CI plot [Chou-Talalay plot] assessing synergism and/or antagonism is illustrated. Fa values of 0, 0.5, and 1 correspond to 0, 50, and 100% killed cells. (FIG. 3A) venetoclax and decitabine; (FIG. 3B) venetoclax and cusatuzumab; (FIG. 3C) decitabine and cusatuzumab; (FIG. 3D) venetoclax, decitabine and cusatuzumab.

(FIG. 4A) venetoclax and decitabine; (FIG. 4B) venetoclax and cusatuzumab; (FIG. 4C) decitabine and cusatuzumab; (FIG. 4D) venetoclax, decitabine and cusatuzumab.

(FIG. 6A) Absolute number of colonies per well for first plating following treatment; (FIG. 6B) Cells harvested from the first plating were re-plated ($2^{nd}$ plating) and colonies per well assessed 14 days later. Data are represented as mean±S.D. Statistics: One-way-ANOVA; Tukey's post-test; *, $P<0.05$; , $P<0.01$; *, $P<0.001$.

FIGS. 7A-7B: Combined venetoclax and cusatuzumab treatment synergistically eliminates LSCs in vitro. Data presented correspond to the data of FIG. 6, normalized to the mean number of colonies per well following vehicle treatment for each patient. (FIG. 7A) first plating; (FIG. 7B) second plating.

(FIG. 8B) Results from P4 and P5.

DETAILED DESCRIPTION

A. Definitions

Figure 1:
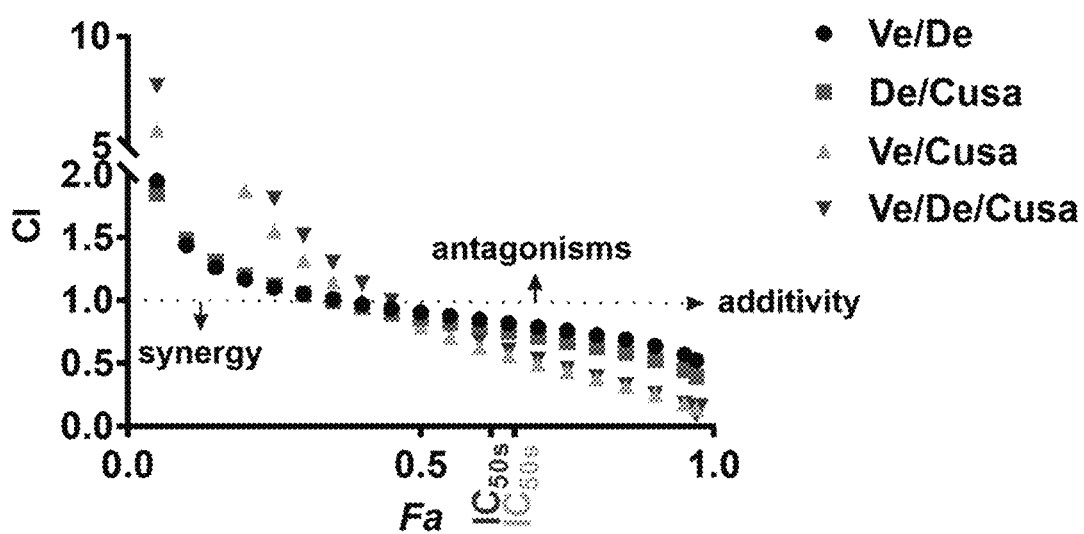
FIG. 1: Cusatuzumab and decitabine co-treatment synergistically eliminates NOMO-1 AML cells. NOMO-1 AML cells were treated with vehicle, cusatuzumab, venetoclax or decitabine alone or in combination in a constant ratio in the presence of carboxyfluorescein succinimidyl ester (CFSE)-labeled NK cells (ratio 1:1). NOMO-1 AML cell numbers per well were counted after 72 hours, the degree of viable cells was determined by Annexin V staining, and the effect of drug treatment was calculated as the ratio of surviving cells to vehicle-treated cells. Combination index (CI) values were calculated, and values between 0 and 10 were plotted against fraction affected (Fa) values. Fa-CI plot [Chou-Talalay plot] assessing synergism and/or antagonism is illustrated. Fa values of 0, 0.5, and 1 correspond to 0, 50, and 100% killed cells. A CI of <1, 1, >1 represents synergism, additivity, and antagonism, respectively. IC$_{50}$s indicates the Fa values reached at the IC$_{50}$ concentrations for the Ve/Cusa (lower Fa) and Ve/De/Cusa (higher Fa) combinations. Ve/De, venetoclax and decitabine; De/Cusa, decitabine and cusatuzumab; Ve/Cusa, venetoclax and cusatuzumab; Ve/De/Cusa, venetoclax and decitabine and cusatuzumab.
Figure 4A:
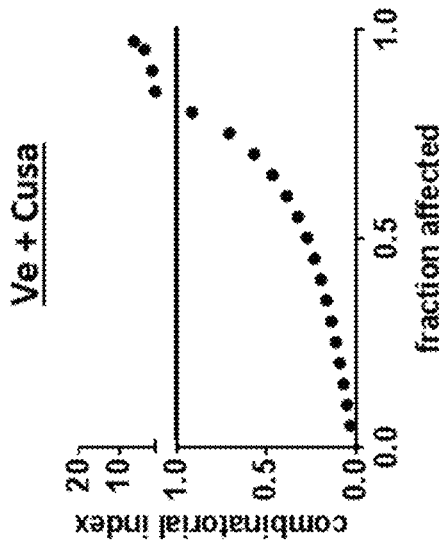
FIGS. 4A-4D: Cusatuzumab and decitabine co-treatment synergistically eliminates MOLM-13 AML cells. MOLM-13 AML cells were treated with vehicle, cusatuzumab, venetoclax or decitabine alone or in combination in a constant ratio in the presence of CFSE-labeled NK cells (ratio 1:1). MOLM-13 AML cell numbers per well were counted after 72 hours, the degree of viable cells was determined by Annexin V staining, and the effect of drug treatment was calculated as the ratio of surviving cells to vehicle-treated cells. Combination index (CI) values were calculated, and values plotted against fraction affected (Fa) values. Fa-CI plot [Chou-Talalay plot] assessing synergism and/or antagonism is illustrated. Fa values of 0, 0.5, and 1 correspond to 0, 50, and 100% killed cells.
Figure 4B:
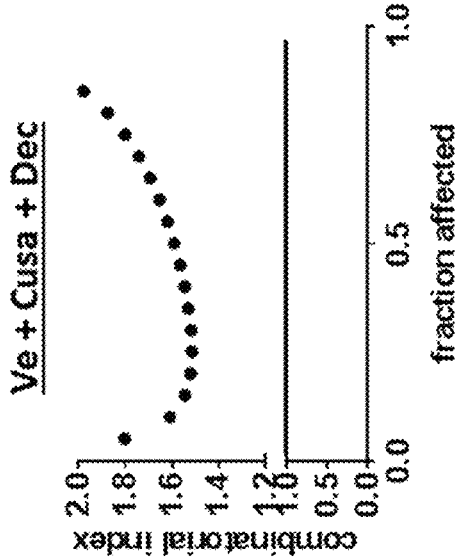
Figure 4C:
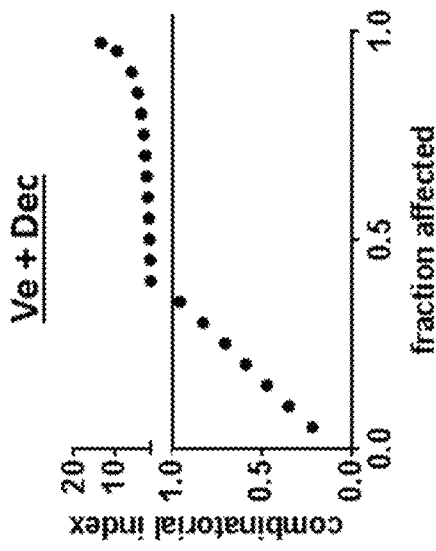
Figure 4D:
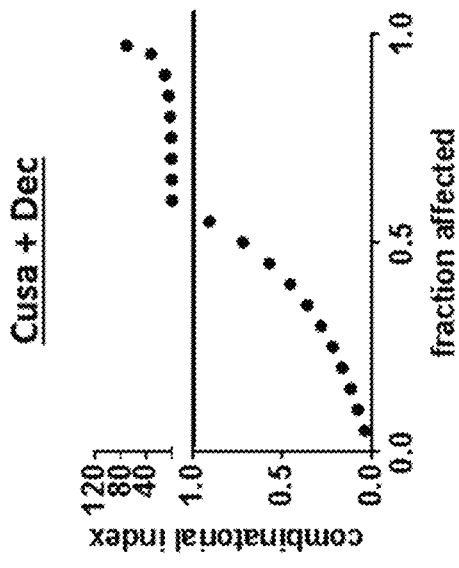
Figure 5:
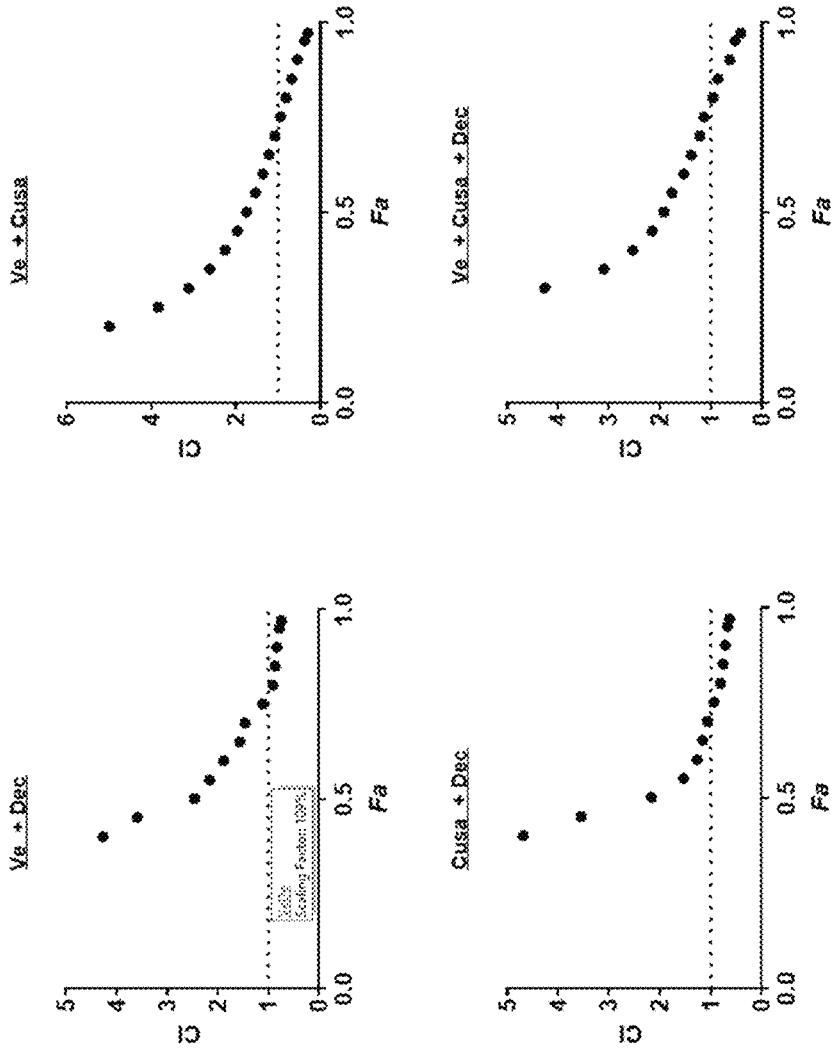
FIG. 5: Cusatuzumab and decitabine co-treatment synergistically eliminates MV4-11 AML cells. MV4-11 AML cells were treated with vehicle, cusatuzumab, venetoclax or decitabine alone or in combination in a constant ratio in the presence of CFSE-labeled NK cells (ratio 1:1). MV4-11 AML cell numbers per well were counted after 72 hours, the degree of viable cells was determined by Annexin V staining, and the effect of drug treatment was calculated as the ratio of surviving cells to vehicle-treated cells. Combination index (CI) values were calculated, and values plotted against fraction affected (Fa) values. Fa-CI plot [Chou-Talalay plot] assessing synergism and/or antagonism is illustrated. Fa values of 0, 0.5, and 1 correspond to 0, 50, and 100% killed cells.

Unless defined otherwise, all technical and scientific terms used herein have the same meaning as is commonly understood by one skilled in the art in the technical field of the invention.

"Combination therapy"—As used herein, the term "combination therapy" refers to a treatment in which a subject, for example a human subject, is given two or more therapeutic agents. The "combinations" described herein are for use in combination therapy. The two or more therapeutic agents are typically administered so as to treat a single disease, herein a cancer or malignancy. The combinations or combination therapies of the present invention comprise antibodies or antigen binding fragments that bind to CD70 and a BCL-2 inhibitor, preferably the small-molecule inhibitor venetoclax or a pharmaceutically acceptable salt thereof. As described elsewhere herein, the agents included in the combination therapies may be co-formulated for administration or may be provided separately, for example as separate compositions, for administration to a subject or patient in need thereof.

"Antibody"—As used herein, the term "antibody" is intended to encompass full-length antibodies and variants thereof, including but not limited to modified antibodies, humanised antibodies, germlined antibodies. The term "antibody" is typically used herein to refer to immunoglobulin polypeptides having a combination of two heavy and two light chains wherein the polypeptide has significant specific immunoreactive activity to an antigen of interest (herein CD70). For antibodies of the IgG class, the antibodies comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region. The light chains of an antibody are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Those skilled in the art will appreciate that heavy chains are classified as gamma, mu, alpha, delta, or epsilon, (γ, µ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. The term "antibody" as used herein encompasses antibodies from any class or subclass of antibody.

"Antigen binding fragment"—The term "antigen binding fragment" as used herein refers to fragments that are parts or portions of a full-length antibody or antibody chain comprising fewer amino acid residues than an intact or complete antibody whilst retaining antigen binding activity. An antigen-binding fragment of an antibody includes peptide fragments that exhibit specific immuno-reactive activity to the same antigen as the antibody (e.g. CD70). The term "antigen binding fragment" as used herein is intended to encompass antibody fragments selected from: an antibody light chain variable domain (VL); an antibody heavy chain variable domain (VH); a single chain antibody (scFv); a F(ab')2 fragment; a Fab fragment; an Fd fragment; an Fv fragment; a one-armed (monovalent) antibody; diabodies, triabodies, tetrabodies or any antigen-binding molecule formed by combination, assembly or conjugation of such antigen binding fragments. The term "antigen binding fragment" as used herein may also encompass antibody fragments selected from the group consisting of: unibodies; domain antibodies; and nanobodies. Fragments can be obtained, for example, via chemical or enzymatic treatment of an intact or complete antibody or antibody chain or by recombinant means.

"Specificity" and "Multispecific antibodies"—The antibodies and antigen binding fragments for use in the combination therapies described herein bind to particular target antigens, e.g. CD70. It is preferred that the antibodies and antigen binding fragments "specifically bind" to their target antigen, wherein the term "specifically bind" refers to the ability of any antibody or antigen binding fragment to preferentially immunoreact with a given target e.g. CD70. The antibodies and antigen binding fragments of the present combinations and methods may be monospecific and contain one or more binding sites which specifically bind a particular target. The antibodies and antigen binding fragments of the present combinations and methods may be incorporated into "multispecific antibody" formats, for example bispecific antibodies, wherein the multispecific antibody binds to two or more target antigens. In order to achieve multiple specificities, "multispecific antibodies" are typically engineered to include different combinations or pairings of heavy and light chain polypeptides with different VH-VL pairs. Multispecific, notably bispecific antibodies, may be engineered so as to adopt the overall conformation of a native antibody, for example a Y-shaped antibody having Fab arms of different specificities conjugated to an Fc region. Alternatively multispecific antibodies, for example bispecific antibodies, may be engineered so as to adopt a non-native conformation, for example wherein the variable domains or variable domain pairs having different specificities are positioned at opposite ends of the Fc region.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. scFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

"Humanising substitutions"—As used herein, the term "humanising substitutions" refers to amino acid substitutions in which the amino acid residue present at a particular position in the VH or VL domain of an antibody is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of the antibodies, defined herein.

"Humanised variants"—As used herein the term "humanised variant" or "humanised antibody" refers to a variant antibody which contains one or more "humanising substitutions" compared to a reference antibody, wherein a portion of the reference antibody (e.g. the VH domain and/or the VL domain or parts thereof containing at least one CDR) has an amino acid derived from a non-human species, and the "humanising substitutions" occur within the amino acid sequence derived from a non-human species.

"Germlined variants"—The term "germlined variant" or "germlined antibody" is used herein to refer specifically to "humanised variants" in which the "humanising substitutions" result in replacement of one or more amino acid residues present at (a) particular position(s) in the VH or VL domain of an antibody with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanised variant" and "germlined variant" are often used interchangeably. Introduction of one or more "humanising substitutions" into a camelid-derived (e.g. llama derived) VH or VL domain results in production of a "humanised variant" of the camelid (llama)-derived VH or VL domain. If the amino acid residues substituted in are derived predominantly or exclusively from a single human germline-encoded VH or VL domain sequence, then the result may be a "human germlined variant" of the camelid (llama)-derived VH or VL domain.

"CD70"—As used herein, the terms "CD70" or "CD70 protein" or "CD70 antigen" are used interchangeably and refer to a member of the TNF ligand family which is a ligand for TNFRSF7/CD27. CD70 is also known as CD27L or TNFSF7. The terms "human CD70 protein" or "human CD70 antigen" or "human CD70" are used interchangeably to refer specifically to the human homolog, including the native human CD70 protein naturally expressed in the human body and/or on the surface of cultured human cell lines, as well as recombinant forms and fragments thereof. Specific examples of human CD70 include the polypeptide having the amino acid sequence shown under NCBI Reference Sequence Accession No. NP_001243, or the extracellular domain thereof.

"BCL-2 family"—As used herein, the term "BCL-2 family" or "BCL-2 protein family" refers to the collection of pro- and anti-apoptotic proteins related to BCL-2, see Delbridge et al. (2016) *Nat Rev Cancer.* 16(2): 99-109. There are at least 16 members of this family categorized into three functional groups: (i) the BCL-2 like proteins (e.g. BCL-2, BCL-$X_L$BCL2L1, BCLW BCL2L2, MCL2, BFL1/BCL2A1); (ii) BAX and BAK; and (iii) the BH3-only proteins (e.g. BIM, PUMA, BAD, BMF, BID, NOXA, HRK, BIK). The BCL-2 family of proteins play an integral role in regulating the intrinsic apoptotic pathway with the anti-apoptotic members of the family (e.g. BCL-2, BCL-$X_L$) typically antagonizing the pro-apoptotic members (e.g. BAX and BIM). Deregulation of BCL-2 family members has been observed in many cancers, for example by gene translocations, amplifications, overexpression and mutations. The downstream effect of this deregulation is frequently apoptosis-resistance, which fuels cancer growth.

"BCL-2"—As used herein, "BCL-2" or the "BCL-2 protein" refers to the first member of the BCL-2 protein family to be identified in humans i.e. B-cell lymphoma 2. The cDNA encoding human BCL-2 was cloned in 1986 and the key role of this protein in inhibiting apoptosis was elucidated in 1988. BCL-2 has been found to be upregulated in several different types of cancer. For example, BCL-2 is activated by the t(14;18) chromosomal translocation in follicular lymphoma. Amplification of the BCL-2 gene has also been reported in different cancers including leukemias (such as CLL), lymphomas (such as B-cell lymphoma) and some solid tumours (e.g. small-cell lung carcinoma). Human BCL-2 is encoded by the BCL2 gene (UniProtKB-P10415) and has the amino acid sequences shown under NCBI Reference Sequences NP_000624.2 and NP_000648.2.

"BCL-2 inhibitor"—As used herein, a BCL-2 inhibitor refers to any agent, compound or molecule capable of specifically inhibiting the activity of BCL-2, in particular an agent, compound or molecule capable of inhibiting the anti-apoptotic activity of BCL-2. Examples of BCL-2 inhibitors suitable for use in the combinations described herein include B cell lymphoma homology 3 (BH3) mimetic compounds (Merino et al. (2018) *Cancer Cell.* 34(6): 879-891). Particular BCL-2 inhibitors include but are not limited to venetoclax, ABT-737 (Oltersdorf, T. et al. (2005) *Nature* 435: 677-681), navitoclax/ABT-263 (Tse, C. et al. (2008) *Cancer Res.* 68: 3421-3428), BM-1197 (Bai, L. et al. (2014) *PLoS ONE* 9: e99404), S44563 (Nemati, F. et al. (2014) *PLoS ONE* 9: e80836), BCL2-32 (Adam, A. et al. (2014) *Blood* 124: 5304), AZD4320 (Hennessy, E. J. et al. (2015) *ACS Medicinal Chemistry annual meeting* https://www.acsmedchem.org/ama/orig/abstracts/mediabstractf-2015.pdf_abstr. 24), and S55746 (International Standard Randomised Controlled Trial Number Registry. ISRCTN http://www.isrctn.com/ISRCTN04804337 (2016). Further examples of BCL-2 inhibitors are described in Ashkenazi, A et al. (2017) *Nature Reviews Drug Discovery* 16: 273-284, incorporated herein by reference.

"Venetoclax"—As used herein, the term "venetoclax" refers to the compound having the chemical structure shown below:

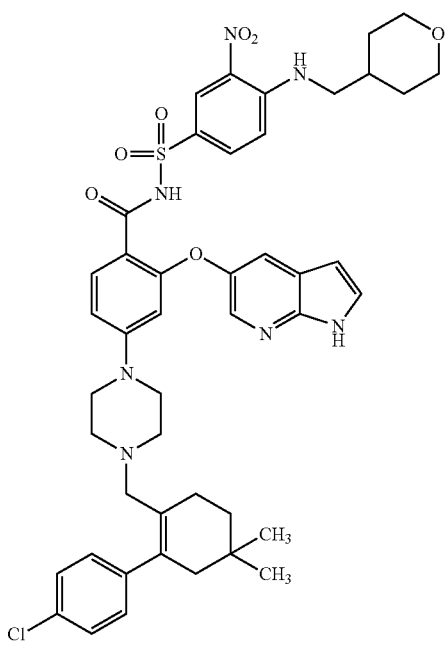 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

This compound is referred to herein as "compound (I)". Venetoclax is a potent, selective, orally-bioavailable inhibitor of the BCL-2 protein. It has the empirical formula $C_{45}H_{50}ClN_7O_7S$ and a molecular weight of 868.44. It has very low aqueous solubility. Venetoclax can be described chemically as 4-(4-{[2-(4-chlorophenyl)-4,4dimethylcyclohex-1-en-1-yl]methyl}piperazin-1-yl)-N-({3-nitro-4-[(tetrahydro-2H-pyran-4ylmethyl)amino]phenyl}sulfonyl)-2-(1H-pyrrolo[2,3-b]pyridin-5-yloxy)benzamide). Alternative names for venetoclax include ABT-199; chemical name 1257044-40-8; GDC-0199.

Venetoclax received approval in 2015 from the US Food and Drug Administration (FDA) for the treatment of adult patients with chronic lymphocytic leukemia (CLL) or small lymphocytic leukemia (SLL) who have received at least one prior therapy. Venetoclax is also approved in the US for use in combination with azacitidine or decitabine or low-dose cytarabine for the treatment of newly-diagnosed acute myeloid leukemia (AML) in adults aged 75 years or older or who have comorbidities that preclude use of intensive induction chemotherapy.

"Myeloid malignancy"—As used herein, the term "myeloid malignancy" refers to any clonal disease of hematopoietic stem or progenitor cells. Myeloid malignancies or myeloid malignant diseases include chronic and acute conditions. Chronic conditions include myelodysplastic syndromes (MDS), myeloproliferative neoplasms (MPN) and chronic myelomonocytic leukemia (CMML), and acute conditions include acute myeloid leukemia (AML).

"Acute myeloid malignancy"—As used herein, "acute myeloid leukemia" or "AML" refers to haematopoietic neoplasms involving myeloid cells. AML is characterised by clonal proliferation of myeloid precursors with reduced differentiation capacity. AML patients exhibit an accumulation of blast cells in the bone marrow. "Blast cells", or simply "blasts", as used herein refers to clonal myeloid progenitor cells exhibiting disrupted differentiation potential. Blast cells typically also accumulate in the peripheral blood of AML patients. Typically AML is diagnosed if the patient exhibits 20% or more blast cells in the bone marrow or peripheral blood.

"Standard intensive chemotherapy"—As used herein, "standard intensive chemotherapy" (also referred to herein as "intensive induction therapy" or "induction therapy") refers to the so-called "7+3" induction chemotherapy characterised by 7 days of high dose cytarabine followed by 3 days of anthracycline administration (e.g. daunorubicin or idarubicin). Standard intensive chemotherapy can be given to eligible newly-diagnosed AML patients with the aim of inducing complete remission of AML, typically with the intention of the patient undergoing a stem cell transplant following successful chemotherapy. As explained herein, not all newly-diagnosed AML patients are eligible for this standard intensive chemotherapy.

"Leukemic stem cells"—As used herein, "leukemic stem cells" or "LSCs" are a subset of the blast cells associated with AML. LSCs are blast cells having stem cell properties such that, if transplanted into an immuno-deficient recipient, they are capable of initiating leukemic disease. LSCs can self-renew by giving rise to leukemia and also partially differentiate into non-LSC conventional blast cells that resemble the original disease but are unable to self-renew. LSCs occur with a frequency in the range of 1 in 10,000 to 1 in 1 million as a proportion of primary AML blast cells (Pollyea and Jordan (2017) *Blood* 129: 1627-1635, incorporated herein by reference). LSCs may be characterised as cells that are CD34+, CD38−, optionally also CD45− and/or CD123+. LSCs may also be characterised as CD45dim, SSClo, CD90+CD34+ cells.

"Anti-cancer agent"—As used herein, an anti-cancer agent refers to any agent that is capable of preventing, inhibiting or treating cancer growth directly or indirectly. Such agents include chemotherapeutic agents, immunotherapeutic agents, anti-angiogenic agents, radionuclides, etc, many examples of which are known to those skilled in the art.

B. Combination Therapy with a CD70 Antibody and a BCL-2 Inhibitor

The present invention provides a combination therapy comprising (i) an antibody or antigen binding fragment thereof that binds to CD70; and (ii) a BCL-2 inhibitor.

As described elsewhere herein, CD70 has already been characterised as an attractive target for anti-cancer therapy.

CD70 is constitutively expressed on many types of hematological malignancies and solid carcinomas and its expression has been linked to poor prognosis for several cancers. Antibodies targeting CD70 have been developed and some have been taken forward into clinical development.

Antibodies targeting CD70 have been found to be particularly effective for the treatment of myeloid malignancies, particularly the treatment of subjects with acute myeloid leukemia (AML). The results from a Phase I/II clinical trial testing the CD70 antibody, ARGX-110, in patients having AML revealed surprising efficacy in this indication, particularly in newly-diagnosed patients classified as unfit for standard intensive chemotherapy (see WO2018/229303). It is particularly notable that in the clinical studies, the CD70 antibody, when used in combination with azacitidine, efficiently reduced leukemic stem cells (LSCs) in the AML patients. Testing of the LSCs isolated from the patients in the trial revealed evidence of increased asymmetric division of LSCs, indicative of differentiation into myeloid cells. Taken together, these results indicate that CD70 antibodies deplete the LSC pool in AML patients thereby increasing the prospect of remission and reducing the risk of relapse.

The present invention combines CD70 antibodies or antigen binding fragments thereof with a BCL-2 inhibitor.

The BCL-2 protein is a member of the BCL-2 family. This family comprises more than 20 proteins. Members of the BCL-2 family are involved in the regulation of the intrinsic apoptosis pathway and play a fundamental role in regulating the balance between cell survival and death.

The BCL-2 protein is an anti-apoptotic member of the BCL-2 family and is up-regulated in many different types of cancer. The overexpression of BCL-2 allows tumour cells to evade apoptosis by sequestering pro-apoptotic proteins. BCL-2 is highly expressed in many hematologic malignancies and is the predominant pro-survival protein in diseases such as chronic lymphocytic leukemia (CLL), follicular lymphoma and mantle cell lymphoma. Inhibition of BCL-2 inhibits the anti-apoptotic or pro-survival activity of this protein. Anti-apoptotic members of the BCL-2 family, including BCL-2, have been reported as overexpressed in primary AML samples (Bogenberger et al. (2014) *Leukemia* 28(2); 1657-65). BCL-2 overexpression has also been reported in leukemic stem cells (LSCs) obtained from AML patients (Lagadinou et al. (2013) *Cell Stem Cell* 12(3); 329-341). Inhibition of BCL-2 in ex vivo LSC populations led to selective eradication of quiescent LSCs (Lagadinou et al. (2013) *Cell Stem Cell* 12(3); 329-341).

Without wishing to be bound by theory, the combination of the present invention is considered to be particularly effective for the treatment of AML due to the combined therapeutic effect of the CD70 antibodies or antigen binding fragments and the BCL-2 inhibitor, particularly the combined effect at the level of the LSCs. The self-renewal capacity of LSCs means that the persistence of these cells is a major factor contributing to disease relapse.

As demonstrated in the Examples, combinations of the invention exhibit synergistic treatment efficacy against AML cells—that is, the level of inhibition induced by the combination is greater than the additive effect of the monotherapies alone. Methods for determining synergistic interaction are familiar to the skilled person and are described in the Examples. A preferred method for determining whether synergistic effects arise from a combination is the Chou-Talalay method (Chou, T C. *Cancer Res.* (2010) 70(2); 440-6, incorporated herein by reference).

The synergistic efficacy of the combinations of the invention translated into potent inhibition of primary LSC cells from AML patients. The combination therapy of the present invention thus targets both the blast cells and the LSC compartment thereby improving the likelihood of disease remission whilst reducing the risk of relapse.

In certain preferred embodiments of the combinations of the invention, the BCL-2 inhibitor is venetoclax or a pharmaceutically acceptable salt thereof. Venetoclax is a small-molecule inhibitor of BCL-2, described in US2010/0305122 (incorporated herein by reference).

By inhibiting BCL-2, venetoclax inhibits the anti-apoptotic or pro-survival activity of this protein. Venetoclax induces apoptosis rapidly in the majority of CLL cells and BCL-2-overexpressing lymphoma cell lines.

Early studies indicated that venetoclax may be useful as a therapy for AML (Konopleva et al. (2016) *Cancer Discov.* 6(10); 1106-17). However, it was found to have limited activity as a monotherapy. Subsequent studies investigated the efficacy of venetoclax in combination with hypomethylating agents, namely azacitidine and decitadine, and these combinations were found to be particularly efficacious (Bogenberger et al. (2015) *Leuk Lymphoma* 56(1): 226-229). Clinical trials have been carried out to test the combination of venetoclax with either azacitidine, decitabine, or low-dose cytarabine (Dinardo et al. (2018) *Lancet Oncol.* 19(2): 216-228; Dinardo et al. (2019) *Blood* 133(1); 7-17). The results of these trials have led to FDA approval for use of venetoclax in combination with azacitidine, decitabine or low-dose cytarabine for the treatment of newly-diagnosed acute myeloid leukemia (AML) in adults who are age 75 years or older, or who have comorbidities that preclude the use of intensive induction chemotherapy.

In certain alternative embodiments of the invention, the BCL-2 inhibitor is a B cell lymphoma homology 3 (BH3) mimetic compound. In certain embodiments, the BCL-2 inhibitor is selected from ABT-737, navitoclax, BM-1197, S44563, BCL2-32, AZD4320 or S55746.

CD70 Antibodies

Antibodies or antigen binding fragments that bind to CD70 and that may be incorporated into any of the combinations described herein include but are not limited to: CD70 antibodies or antigen binding fragments that inhibit interaction of CD70 with CD27; CD70 antibodies or antigen binding fragments that compete with CD27 for CD70 binding; CD70 antibodies or antigen binding fragments that inhibit CD70-induced CD27 signalling; CD70 antibodies or antigen binding fragments that inhibit Treg activation and/or proliferation; CD70 antibodies or antigen binding fragments that deplete CD70-expressing cells; CD70 antibodies or antigen binding fragments that induce lysis of CD70-expressing cells; CD70 antibodies or antigen binding fragments that possess ADCC, CDC functionality, and/or induce ADCP.

Exemplary CD70 antibodies are ARGX-110 described in WO2012/123586 (incorporated herein by reference), SGN-70 (WO2006/113909, and McEarChern et al. (2008) *Clin Cancer Res.* 14(23):7763, both incorporated herein by reference) and those CD70 antibodies described in WO2006/044643 and WO2007/038637 (each incorporated herein by reference).

WO2006/044643 describes CD70 antibodies containing an antibody effector domain which can mediate one or more of ADCC, ADCP or CDC and either exert a cytostatic or cytotoxic effect on a CD70-expressing cancer or exert an immunosuppressive effect on a CD70-expressing immunological disorder in the absence of conjugation to a cytostatic or cytotoxic agent. The antibodies exemplified therein are based on the antigen-binding regions of two monoclonal antibodies, denoted 1F6 and 2F2.

WO2007/038637 describes fully human monoclonal antibodies that bind to CD70. These antibodies are characterised by binding to human CD70 with a $K_D$ of $1\times10^{-7}$ M or less. The antibodies also bind to, and are internalised by, renal cell carcinoma tumor cell lines which express CD70, such as 786-O.

ARGX-110 is an IgG1 anti-CD70 antibody, also known as cusatuzumab. ARGX-110 has been shown to inhibit the interaction of CD70 with its receptor CD27 (Silence et al. (2014) *MAbs*. March-April; 6(2):523-32, incorporated herein by reference). In particular, ARGX-110 has been shown to inhibit CD70-induced CD27 signalling. Levels of CD27 signalling may be determined by, for example, measurement of serum soluble CD27 as described in Riether et al. (*J. Exp. Med*. (2017) 214(2); 359-380) or of IL-8 expression as described in Silence et al. (*MAbs* (2014) 6(2): 523-32). Without being bound by theory, inhibiting CD27 signalling is thought to reduce activation and/or proliferation of Treg cells, thereby reducing inhibition of anti-tumour effector T cells. ARGX-110 has also been demonstrated to deplete CD70-expressing tumour cells. In particular, ARGX-110 has been shown to lyse CD70-expressing tumour cells via antibody dependent cell-mediated cytotoxicity (ADCC) and complement dependent cytotoxicity (CDC), and also to increase antibody dependent cellular phagocytosis (ADCP) of CD70-expressing cells (Silence et al., ibid).

The CDR, VH and VL amino acid sequences of ARGX-110 or cusatuzumab are shown in the table below.

TABLE 1

| ARGX-110 | Sequence | SEQ ID NO. |
|---|---|---|
| HCDR1 | VYYMN | 1 |
| HCDR2 | DINNEGGTTYYADSVKG | 2 |
| HCDR3 | DAGYSNHVPIFDS | 3 |
| VH | EVQLVESGGGLVQPGGSLRLSCAASGF TFSVYYMNWVRQAPGKGLEWVSDINNE GGTTYYADSVKGRFTISRDNSKNSLYL QMNSLRAEDTAVYYCARDAGYSNHVPI FDSWGQGTLVTVSS | 4 |
| LCDR1 | GLKSGSVTSDNFPT | 5 |
| LCDR2 | NTNTRHS | 6 |
| LCDR3 | ALFISNPSVE | 7 |
| VL | QAVVTQEPSLTVSPGGTVTLTCGLKSG SVTSDNFPTWYQQTPGQAPRLLIYNTN TRHSGVPDRFSGSILGNKAALTITGAQ ADDEAEYFCALFISNPSVEFGGGTQLT VLG | 8 |

In certain embodiments, the antibody or antigen binding fragment thereof that binds to CD70 comprises a variable heavy chain domain (VH) and a variable light chain domain (VL) wherein the VH and VL domains comprise the CDR sequences:
HCDR3 comprising or consisting of SEQ ID NO: 3;
HCDR2 comprising or consisting of SEQ ID NO: 2;
HCDR1 comprising or consisting of SEQ ID NO: 1;
LCDR3 comprising or consisting of SEQ ID NO: 7;
LCDR2 comprising or consisting of SEQ ID NO: 6; and
LCDR1 comprising or consisting of SEQ ID NO: 5.

In certain embodiments, the antibody or antigen binding fragment thereof that binds to CD70, optionally the antibody or antigen binding fragment having the CDR sequences shown above, is an IgG, preferably an IgG1. In certain embodiments, the antibody or antigen binding fragment thereof that binds to CD70 comprises a variable heavy chain domain (VH domain) comprising or consisting of a sequence at least 70%, at least 80%, at least 90% or at least 95% identical to SEQ ID NO: 4 and a variable light chain domain (VL domain) comprising or consisting of a sequence at least 70%, at least 80%, at least 90% or at least 95% identical to SEQ ID NO: 8. In certain embodiments, the antibody molecule that binds to CD70 comprises a variable heavy chain domain (VH domain) comprising or consisting of SEQ ID NO: 4 and a variable light chain domain (VL domain) comprising or consisting of SEQ ID NO: 8. For embodiments wherein the VH and/or VL domains are defined as having a particularly percentage identity to a reference sequence, the VH and/or VL domains may retain the CDR sequences of the reference sequence. In particular, the CD70 antibodies or antigen binding fragments defined herein with reference to SEQ ID NOs: 4 and 8 may retain the CDR sequences as represented by SEQ ID NOs: 1-3 and 5-7.

CD70 antibody or antigen binding fragments thereof that may be incorporated into the combinations described herein include antibody drug conjugates (ADCs). ADCs are antibodies attached to active agents, for example auristatins and maytansines or other cytotoxic agents. Certain ADCs maintain antibody blocking and/or effector function (e.g. ADCC, CDC, ADCP) while also delivering the conjugated active agent to cells expressing the target (e.g. CD70). Examples of anti-CD70 ADCs include vorsetuzumab mafodotin (also known as SGN-75, Seattle Genetics), SGN-70A (Seattle Genetics), and MDX-1203/BMS936561 (Bristol-Myers Squibb), each of which may be used in accordance with the invention. Suitable anti-CD70 ADCs are also described in WO2008074004 and WO2004073656, each of which is incorporated herein by reference.

Venetoclax

In certain preferred embodiments of the invention, the CD70 antibodies or antigen binding fragments described herein are combined with venetoclax or a pharmaceutically acceptable salt thereof. Venetoclax is a small molecule inhibitor of BCL-2 as described elsewhere herein.

Venetoclax for use in the combination therapies described herein may be provided in any suitable form such that it effectively inhibits the BCL-2 protein. Such forms include but are not limited to any suitable polymorphic, amorphous or crystalline forms or any isomeric or tautomeric forms. In certain embodiments, the combination therapies described herein comprise venetoclax synthesised according to the process described in US2010/0305122 (incorporated herein by reference). In alternative embodiments, the combination therapies described herein comprise venetoclax according to the forms or synthesised according to the processes described in any one of EP3333167, WO2017/156398, WO2018/029711, CN107089981 (A), WO2018/069941, WO2017/212431, WO2018/009444, CN107648185 (A), WO2018/167652, WO2018/157803, CZ201769 (each incorporated herein by reference). In certain embodiments, the combination therapies described herein comprise venetoclax in any of the crystalline or salt forms described in WO2012/071336 (incorporated herein by reference).

Pharmaceutically acceptable salts for use in accordance with the present invention include salts of acidic or basic groups. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Pharmaceutically acceptable salts may be formed with various amino acids. Suitable base salts include, but are not limited to, aluminum, calcium, lithium, magnesium, potassium, sodium, zinc, and diethanolamine salts.

Venetoclax for use in the combination therapies described herein may also be provided in the form of a hydrate, anhydrate or solvate.

Venetoclax is marketed and sold by AbbVie Inc and Genentech under the trade name Venclexta®. In certain embodiments, the combinations described herein comprise an antibody or antigen binding fragment thereof that binds CD70 and Venclexta®.

Additional Agents

The combinations of the present invention may include one or more additional agents, for example one or more additional anti-cancer agents.

In certain embodiments, the combination comprises one or more "nucleoside metabolic inhibitors" (NMIs). NMIs are molecules that interfere with epigenetic modification (e.g. methylation, demethylation, acetylation, or deacetylation) of nucleotides (DNA and/or RNA). Examples of nucleoside metabolic inhibitors include hypomethylating agents (HMAs), isocitrate dehydrogenase (IDH) inhibitors, histone deacetylase (HDAC) inhibitors, and bromodomain and extraterminal (BET) inhibitors. Preferred nucleoside metabolic inhibitors are hypomethylating agents. Hypomethylating agents inhibit normal methylation of DNA and/or RNA. Examples of hypomethylating agents are azacitidine, decitabine and guadecitabine.

In preferred embodiments, the combinations of the invention additionally comprise azacitidine (also referred to herein as azacytidine, AZA or aza). Thus, in preferred embodiments, the present invention provides a combination comprising (i) an antibody or antigen binding fragment thereof that binds to CD70; (ii) venetoclax or a pharmaceutically acceptable salt thereof; and (iii) azacitidine.

In further preferred embodiments, the combinations of the invention additionally comprise decitabine. Thus, in preferred embodiments, the present invention provides a combination comprising (i) an antibody or antigen binding fragment thereof that binds to CD70; (ii) venetoclax or a pharmaceutically acceptable salt thereof; and (iii) decitabine.

Azacitidine is an analogue of cytidine and decitabine is its deoxy derivative. Azacitdine and decitabine are inhibitors of DNA methyltransferases (DNMT) known to upregulate gene expression by promoter hypomethylation. Such hypomethylation disrupts cell function, thereby resulting in cytotoxic effects.

In certain embodiments, the combinations of the present invention additionally comprise cytarabine. Cytarabine (also known as "cytosine arabinose" or "ara-C") is a chemotherapeutic drug commonly used to treat AML. High-dose cytarabine forms part of the "7+3" standard induction chemotherapy typically used for newly-diagnosed AML patients. Low-dose cytarabine may be used for AML patients who are not eligible for the standard induction chemotherapy. For example, low-dose cytarabine is prescribed in combination with venetoclax for newly-diagnosed AML patients ineligible for standard induction chemotherapy. The combinations of the present invention may additionally comprise low-dose cytarabine.

In certain embodiments, the combinations of the present invention comprise an additional anti-cancer agent. The one or more additional cancer agents may be selected from any agents suitable for the treatment of myeloid malignancies, preferably AML. Preferred agents may be selected from: selectin inhibitors (e.g. GMI-1271); FMS-like tyrosine kinase receptor 3 (FLT3) inhibitors (e.g. midostaurin or gilteritinib); cyclin-dependent kinase inhibitors; aminopeptidase inhibitors; JAK/STAT inhibitors; cytarabine; fludarabine; anthracycline compounds (e.g. daunorubicin, idarubicin); doxorubicin; hydroxyurea; Vyxeos; IDH1 or IDH2 inhibitors such as Idhifa (or Enasidenib) or Tibsovo (or ivosidenib); Smoothened inhibitors such as Glasdegib; BET bromodomain inhibitors; CD123 or CD33 targeting agents; HDAC inhibitors; LSC targeting agents; AML bone marrow niche targeting agents; NEDD8-activating enzyme inhibitors such as Pevonedistat; G-CSF, and topoisomerase inhibitors such as mitoxantrone, selinexor and etoposide.

Formulation of the Combination

The agents of the combinations described herein may be combined or formulated in any manner allowing the combination therapy to be administered to a subject or patient in need thereof, preferably a human subject or patient in need thereof. The combination may be formulated for single dose administration or for multiple dose administration.

In certain embodiments, the agents of the combinations may be co-formulated i.e. formulated as a single pharmaceutical composition. For embodiments wherein the agents are co-formulated, the combination or composition is suitable for simultaneous administration of the agents.

In preferred embodiments, the agents of the combinations described herein are formulated as separate compositions or pharmaceutical compositions. For embodiments wherein the agents are formulated separately, the possibility exists for simultaneous or separate administration of the different agents or compositions. If the different compositions are administered separately, there may be sequential administration of the agents in any preferred order. The interval between administration of the agents may be any suitable time interval. The administration of the different compositions may be carried out once (for a single dose administration) or repeatedly (for a multiple dose administration).

The CD70 antibodies or antigen binding fragments of the combinations described herein may be formulated using any suitable pharmaceutical carriers, adjuvants and/or excipients. Techniques for formulating antibodies for human therapeutic use are well known in the art and are reviewed, for example, in Wang et al. (2007) *Journal of Pharmaceutical Sciences*, 96:1-26, the contents of which are incorporated herein in their entirety. Pharmaceutically acceptable excipients that may be used to formulate the antibody compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

The BCL-2 inhibitor (preferably venetoclax or a pharmaceutically acceptable salt thereof) may be formulated using any suitable pharmaceutical carriers, adjuvants and/or excipients. Suitable agents include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

In certain embodiments, the compositions are formulated for administration to a subject via any suitable route of administration including but not limited to intramuscular, intravenous, intradermal, intraperitoneal injection, subcutaneous, epidural, nasal, oral, rectal, topical, inhalational, buccal (e.g., sublingual), and transdermal administration. In certain embodiments, the compositions are formulated as aqueous solutions, tablets, capsules, powders or any other suitable dosage form.

Excipients for preparation of compositions comprising a BCL-2 inhibitor (preferably venetoclax) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a BCL-2 inhibitor (preferably venetoclax) to be administered orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a BCL-2 inhibitor (preferably venetoclax) to be administered osmotically include, for example, chlorofluorohydrocarbons, ethanol, water and mixtures thereof. Excipients for preparation of compositions comprising a BCL-2 inhibitor (preferably venetoclax) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

For embodiments wherein the agents of the combination are formulated separately i.e. as separate compositions, the separate compositions may be formulated for the same route of administration. For embodiments wherein the agents of the combination are formulated separately i.e. as separate compositions, the separate compositions may be formulated for different routes of administration. For example, the CD70 antibody or antigen binding fragment may be formulated for intravenous administration and the BCL-2 inhibitor (preferably venetoclax) may be formulated for oral administration.

As noted above, the combination therapies of the present invention may comprise Venclexta®. Venclexta® is a venetoclax product marketed and sold by AbbVie Inc and Genentech. Venclexta® tablets for oral administration are supplied as pale yellow or beige tablets that contain 10, 50, or 100 mg venetoclax as the active ingredient. Each tablet also contains the following inactive ingredients: copovidone, colloidal silicon dioxide, polysorbate 80, sodium stearyl fumarate, and calcium phosphate dibasic. In addition, the 10 mg and 100 mg coated tablets include the following: iron oxide yellow, polyvinyl alcohol, polyethylene glycol, talc, and titanium dioxide. The 50 mg coated tablets also include the following: iron oxide yellow, iron oxide red, iron oxide black, polyvinyl alcohol, talc, polyethylene glycol and titanium dioxide. For embodiments wherein a CD70 antibody or antigen binding fragment thereof is combined with Venclexta®, the CD70 antibody or antigen binding fragment may be formulated for intravenous administration whilst the Venclexta® is provided as one or more of the tablet forms described above.

For combinations of the invention comprising or consisting of agents in addition to the CD70 antibodies or antigen binding fragments and a BCL-2 inhibitor (preferably venetoclax), the one or more additional agents may be formulated for administration via the same route or via a different route as compared with the other agents. For example, in preferred embodiments wherein the combination includes (i) an antibody or antigen binding fragment thereof that binds to CD70; (ii) venetoclax or a pharmaceutically acceptable thereof; and (iii) azacitidine, the antibody or antigen binding fragment may be administered intravenously, the venetoclax or pharmaceutically acceptable salt thereof may be administered orally whilst the azacitidine may be administered subcutaneously via injection. In preferred embodiments wherein the combination includes (i) an antibody or antigen binding fragment thereof that binds to CD70; (ii) venetoclax or a pharmaceutically acceptable thereof; and (iii) decitabine, the antibody or antigen binding fragment may be administered intravenously, the venetoclax or pharmaceutically acceptable salt thereof may be administered orally whilst the decitabine may be administered subcutaneously via injection.

C. Methods of Treatment

The combination therapies described in accordance with the first aspect of the invention can be used in methods of treating a malignancy, particularly a myeloid malignancy, in a human subject.

The present invention provides an antibody or antigen binding fragment thereof that binds to CD70 for use in the treatment of a malignancy, particularly a myeloid malignancy, in a human subject, wherein the antibody or antigen binding fragment thereof is administered in combination with a BCL-2 inhibitor. The present invention also provides a BCL-2 inhibitor for use in the treatment of a malignancy, particularly a myeloid malignancy, in a human subject, wherein the BCL-2 inhibitor is administered in combination with an antibody or antigen binding fragment that binds to CD70.

In preferred embodiments, the BCL-2 inhibitor is venetoclax or a pharmaceutically acceptable salt thereof.

The present invention further provides a combination in accordance with the first aspect of the invention for use in the treatment of a malignancy, particularly a myeloid malignancy, in a human subject.

In a yet further aspect, the present invention provides a method for treating a malignancy, particularly a myeloid malignancy, in a human subject, said method comprising administering to the subject a combination in accordance with the first aspect of the invention. The invention also provides a method for treating a malignancy, particularly a myeloid malignancy, in a human subject, said method comprising the steps of (i) administering to the subject an antibody or antigen binding fragment thereof that binds to CD70; and (ii) administering to the subject a BCL-2 inhibitor, preferably venetoclax or a pharmaceutically acceptable salt thereof. Steps (i) and (ii) of the method may be performed in either order.

All embodiments described above in relation to the combination of the first aspect of the invention are equally applicable to the methods described herein.

The term "malignancy" encompasses diseases in which abnormal cells proliferate in an uncontrolled manner and invade the surrounding tissues. Malignant cells that have entered the body's blood and lymph systems are capable of travelling to distal sites in the body and seeding at secondary locations. In certain embodiment, the methods described herein are for treating malignancies comprising the production of cancer progenitor or stem cells expressing CD70, CD27, or both. As noted elsewhere herein, upregulated CD70 expression has been detected in different types of cancers including renal cell carcinomas, metastatic breast cancers, brain tumours, leukemias, lymphomas and nasopharyngeal carcinomas. Co-expression of CD70 and CD27 has also been detected in malignancies of the hematopoietic lineage including acute lymphoblastic lymphoma and T cell lymphoma. In certain embodiments, the methods described herein are for the treatment of any of the aforementioned malignancies associated with CD70 expression, CD27 expression or both.

In particular embodiments, the methods described herein are for treating myeloid malignancies, wherein a myeloid malignancy refers to any clonal disease of hematopoietic stem or progenitor cells. The myeloid malignancy treated in accordance with the methods of the invention may be a newly-diagnosed myeloid malignancy or a relapsed/refractory myeloid malignancy.

In certain embodiments, the myeloid malignancy is selected from: acute myeloid leukemia (AML); myelodysplastic syndromes (MDS); myeloproliferative neoplasms (MPN); chronic myeloid leukemia (CML); and chronic myelomonocytic leukemias (CMML). In preferred embodiments, the myeloid malignancy is acute myeloid leukemia (AML).

Myeloid malignancies can be categorised and diagnosed according to the WHO 2008 classification, taken in combination with the 2016 update to this classification, see in particular Arber et al. (2016) *Blood* 127(20):2391-2405, incorporated herein by reference.

Acute myeloid leukemia (AML) refers to haematopoietic neoplasms involving myeloid cells. AML is characterised by clonal proliferation of myeloid precursors with reduced differentiation capacity. AML patients exhibit an accumulation of blast cells in the bone marrow. Blast cells also accumulate in the peripheral blood of AML patients. Typically AML is diagnosed if the patient exhibits 20% or more blast cells in the bone marrow or peripheral blood.

According to the WHO classification, AML in general encompasses the following subtypes: AML with recurrent genetic abnormalities; AML with myelodysplasia-related changes; therapy-related myeloid neoplasms; myeloid sarcoma; myeloid proliferations related to Down syndrome; blastic plasmacytoid dendritic cell neoplasm; and AML not otherwise categorized (e.g. acute megakaryoblastic leukemia, acute basophilic leukemia).

AML can also be categorised according to the French-American-British (FAB) classification, encompassing the subtypes: M0 (acute myeloblastic leukemia, minimally differentiated); M1 (acute myeloblastic leukemia, without maturation); M2 (acute myeloblastic leukemia, with granulocytic maturation); M3 (promyelocytic, or acute promyelocytic leukemia (APL)); M4 (acute myelomonocytic leukemia); M4eo (myelomonocytic together with bone marrow eosinophilia); M5 (acute monoblastic leukemia (M5a) or acute monocytic leukemia (M5b)); M6 (acute erythroid leukemias, including erythroleukemia (M6a) and very rare pure erythroid leukaemia (M6b)); or M7 (acute megakaryoblastic leukemia).

As used herein, "AML" refers to any of the conditions encompassed by the WHO and/or FAB classifications, unless specified otherwise. Certain AML subtypes are considered to be of more favourable prognosis, some of intermediate prognosis and some of poor prognosis. The skilled person is aware of which subtypes would fall into which risk category.

Myelodysplastic syndrome (MDS) is characterised by dysplasia, cytopenia and/or abnormal changes in bone marrow cellularity and/or myeloid differentiation, for example increased blast cell infiltration. According to the WHO classification, MDS in general encompasses the following subtypes: MDS with single lineage dysplasia (previously called "refractory cytopenia with unilineage dysplasia", which includes refractory anemia, refractory neutropenia, and refractory thrombocytopenia); MDS with ring sideroblasts, which includes subgroups with single lineage dysplasia and multilineage dysplasia (previously called "refractory anemia with ring sideroblasts"); MDS with multilineage dysplasia (previously called "refractory cytopenia with multilineage dysplasia"); MDS with excess blasts (MDS-EB, previously called "refractory anemia with excess blasts"), which can be further subclassified into MDS-EB-1 and MDS-EB-2 based on blast percentages; MDS with isolated del(5q); and MDS, unclassified.

MDS can also be categorised according to the French-American-British (FAB) classification, encompassing the subtypes: M9980/3 (refractory anaemia (RA)); M9982/3 (refractory anaemia with ring sideroblasts (RARS)); M9983/3 (refractory anaemia with excess blasts (RAEB)); M9984/3 (refractory anaemia with excess blasts in transformation (RAEB-T)); and M9945/3 (chronic myelomonocytic leukemia (CMML)).

As used herein, "MDS" refers to any of the conditions encompassed by the WHO and/or FAB classifications, unless specified otherwise. For both AML and MDS, the WHO categorisation is preferred herein.

Myeloproliferative neoplasms (MPN) are similar to MDS but according to the WHO classification, MPN in general encompasses the following subtypes: chronic myeloid leukemia (CML); chronic neutrophilic leukemia (CNL); polycythemia vera (PV); primary myelofibrosis (PMF); Essential thrombocythemia (ET); chronic eosinophilic leukemia, not otherwise specified; and MPN unclassifiable.

Chronic myelomonocytic leukemia (CMML) and atypical chronic myeloid leukemia (aCML) fall within the category of MDS/MPN disorders according to the WHO classification, for the reason that they represent myeloid neoplasms with clinical, laboratory and morphologic features that overlap between MDS and MPN.

Patient Characteristics

The patients or subjects treated in accordance with the methods described herein, particularly those having AML, may have newly-diagnosed disease, relapsed disease or primary refractory disease.

A standard approach to treatment for newly-diagnosed AML patients is the "standard 7+3 intensive chemotherapy" approach characterised by 7 days of high dose cytarabine followed by 3 days of anthracycline administration (e.g. daunorubicin or idarubicin). Intensive chemotherapy is given with the aim of inducing complete remission of AML, typically with the intention of the patient undergoing a stem cell transplant following successful chemotherapy.

Standard intensive chemotherapy is associated with significant toxicity and side-effects, meaning it is not suitable for patients unable to tolerate these effects. These patients are termed "ineligible for standard intensive chemotherapy". A patient may be ineligible for standard intensive chemotherapy because, for example, they exhibit one or more comorbidities indicating they would not tolerate the toxicity, or the prognostic factors characterising their disease indicate an unfavourable outcome of standard intensive chemotherapy. Determination of an individual patient's eligibility for standard intensive chemotherapy would be performed by a clinician taking into account the individual patient's medical history and clinical guidelines (e.g. the National Comprehensive Cancer Network (NCCN) guidelines, incorporated herein by reference). AML patients over the age of 60 are often assessed as ineligible for standard intensive chemotherapy, with other factors to be considered including the cytogenetics and/or molecular abnormalities of the AML being treated.

A patient ineligible for standard intensive chemotherapy may instead receive chemotherapy of reduced intensity, such as low dose cytarabine (LDAC). Patients ineligible for standard intensive chemotherapy and for whom LDAC is not appropriate can receive best supportive care (BSC), including hydroxyurea (HU) and transfusion support.

Patients or subjects treated in accordance with the methods described herein may be those classified as "ineligible for standard intensive chemotherapy". The combinations of the invention comprise targeted therapies that may be predicted to have fewer side-effects. As such, patients deemed ineligible for standard intensive chemotherapy, for any of the reasons identified above, may be treated with the combinations according to the present invention.

As discussed above, venetoclax is authorised in the US for use in combination with azacitidine, decitabine or low-dose cytarabine for the treatment of newly-diagnosed AML in adults who are aged 75 years or older or who have comorbidities that preclude use of intensive induction chemotherapy. Thus, in certain embodiments, particularly embodiments wherein the BCL-inhibitor is venetoclax or a pharmaceutically acceptable salt thereof, patients or subjects treated in accordance with the methods described herein are newly-diagnosed AML patients aged 75 years or older. In further embodiments, patients or subjects treated in accordance with the methods described herein are newly-diagnosed AML patients having comorbidities that preclude use of intensive induction therapy. Patients having a comorbidity precluding use of intensive induction chemotherapy may be classified as such based on at least one of the following criteria: baseline Eastern Cooperative Oncology Group (ECOG) performance status of 2-3, severe cardiac or pulmonary comorbidity, moderate hepatic impairment, or CLcr<45 ml/min. Such embodiments are particularly preferred when the BCL-2 inhibitor in the combination according to the invention is venetoclax or a pharmaceutically acceptable salt thereof.

Patients or subjects treated in accordance with the methods described herein may be eligible for other treatments, for example standard intensive chemotherapy, but may receive the combination therapies described herein as an alternative treatment option. For example, patients or subjects treated in accordance with the methods described herein may be newly-diagnosed AML patients otherwise eligible for standard intensive chemotherapy.

Additional Agents for Treatment

The methods described herein may include administration of one or more additional therapeutic agents, for example, additional anti-cancer agents. In certain embodiments, the methods comprise the administration of one or more agents for use in treating myeloid malignancies, for example agents suitable for use in treating AML. Such agents include but are not limited to: selectin inhibitors (e.g. GMI-1271); FMS-like tyrosine kinase receptor 3 (FLT3) inhibitors (e.g. midostaurin or gilteritinib); cyclin-dependent kinase inhibitors; aminopeptidase inhibitors; JAK/STAT inhibitors; cytarabine; fludarabine; anthracycline compounds (e.g. daunorubicin, idarubicin); doxorubicin; hydroxyurea; Vyxeos; IDH1 or IDH2 inhibitors such as Idhifa (or Enasidenib) or Tibsovo (or ivosidenib); Smoothened inhibitors such as Glasdegib; BET bromodomain inhibitors; CD123 or CD33 targeting agents; HDAC inhibitors; LSC targeting agents; AML bone marrow niche targeting agents; NEDD8-activating enzyme inhibitors such as Pevonedistat; G-CSF, and topoisomerase inhibitors such as mitoxantrone, selinexor and etoposide.

In preferred embodiments, the methods described herein comprise administration of a further agent that is a nucleoside metabolic inhibitor, preferably a hypomethylating agent. Particularly preferred hypomethylating agents are azacitidine and decitabine. As described herein above, in certain embodiments the combinations of the invention comprising (i) a CD70 antibody or antigen binding fragment thereof; and (ii) a BCL-2 inhibitor, preferably venetoclax or a pharmaceutically acceptable salt, may be formulated so as to include additional agents, for example azacitidine or decitabine.

Alternatively, for embodiments wherein the combination consists of (i) an antibody or antigen binding fragment that binds to CD70; and (ii) a BCL-2 inhibitor, preferably venetoclax or a pharmaceutically acceptable salt thereof, the methods wherein the combination is administered to a subject, may comprise a further step of administering the additional agent, for example azacitidine or decitabine. Thus, in a preferred embodiment, the present invention provides a method for treating a myeloid malignancy, preferably AML, in a human subject, said method comprising administering to the subject: (i) an antibody or antigen binding fragment thereof that binds to CD70; (ii) a BCL-2 inhibitor, preferably venetoclax or a pharmaceutically acceptable salt thereof; and (iii) azacitidine or decitabine. Also provided herein is a combination for use in treating a myeloid malignancy, preferably AML, in a human subject, said combination comprising: (i) an antibody or antigen binding fragment thereof that binds to CD70; (ii) a BCL-2 inhibitor, preferably venetoclax or a pharmaceutically acceptable salt thereof; and (iii) azacitidine or decitabine.

Dosing

As demonstrated in the Examples, combinations of the invention exhibit synergistic treatment efficacy against AML cells—that is, the level of inhibition induced by the combination is greater than the additive effect of the monotherapies alone.

Methods for determining synergistic interaction are familiar to the skilled person and are described in the Examples. A preferred method for determining whether synergistic effects arise from a combination is the Chou-Talalay method (Chou, T C. Cancer Res. 2010 Jan. 15; 70(2):440-6, incorporated herein by reference).

According to the Chou-Talalay method, a CI of <1 shows synergy, CI=1 shows an additive effect, and a CI>1 shows antagonism. As presented in FIG. 1, the presence and extent of the synergy arising from combinations of the invention varies according to the strength of the inhibitory effect of the combination. The strength of the combination's inhibitory effect itself is dependent on the total concentration of the combination.

Preferably, therefore, in embodiments of all aspects of the invention, the dose at which the CD70 antibody or antigen binding fragment thereof is administered and/or provided in the combination, and the dose at which the BCL-2 inhibitor is administered and/or provided in the combination, are each selected such that the combination provides synergistic treatment—that is, where the combination exhibits a CI of less than 1 as determined by the Chou-Talalay method. Preferably the doses are such that the combination exhibits a CI of less than 0.5.

Preferably, in certain embodiments, the dose at which the CD70 antibody or antigen binding fragment thereof is administered and/or provided in the combination, and the dose at which the BCL-2 inhibitor is administered and/or provided in the combination, are each selected such that the combination exhibits a CI of less than 1 and Fa of >0.5, as determined by the Chou-Talalay method.

As shown in the Examples, synergy was also observed for a combination of an anti-CD70 antibody (ARGX-110), a BCL-2 inhibitor (venetoclax) and an HMA (decitabine). Therefore, in certain preferred embodiments of aspects of the invention where the combination includes an HMA, the dose at which the CD70 antibody or antigen binding fragment thereof is administered and/or provided in the combination, the dose at which the BCL-2 inhibitor is administered and/or provided in the combination, and the dose at which the HMA is administered and/or provided in the combination are each selected such that the combination provides synergistic efficacy in treatment.

It has been found that CD70 antibodies, particularly ARGX-110, are effective for the treatment of myeloid malignancy, particularly AML, at relatively low dose. Therefore, in certain embodiments of all methods of the invention the CD70 antibody or antigen binding fragment thereof is administered at a dose in the range from 0.1 mg/kg to 25 mg/kg per dose, for example in the range of from 0.1 mg/kg to 20 mg/kg. In certain embodiments, the CD70 antibody or antigen binding fragment thereof is administered at a dose in the range from 1 mg/kg to 20 mg/kg per dose. Ranges described herein include the end points of the range unless indicated otherwise—for example, administration at a dose in the range of 0.1-25 mg/kg includes administration at a dose of 0.1 mg/kg and administration at a dose of 25 mg/kg, as well as all doses between the two end points.

In certain embodiments of methods of the invention, the CD70 antibody or antigen binding fragment thereof is administered at a dose in the range from 0.1 mg/kg to 15 mg/kg. In certain embodiments the CD70 antibody or antigen binding fragment thereof is administered at a dose in the range from 0.5 mg/kg to 2 mg/kg. In certain embodiments the CD70 antibody or antigen binding fragment thereof is administered at a dose of 1 mg/kg, 3 mg/kg, 10 mg/kg, or 20 mg/kg. In certain preferred embodiments the CD70 antibody or antigen binding fragment thereof is administered at a dose of 1 mg/kg. In certain preferred embodiments the CD70 antibody or antigen binding fragment thereof is administered at a dose of 10 mg/kg.

In certain embodiments, multiple doses of the CD70 antibody or antigen binding fragment are administered. In certain such embodiments, each dose of the CD70 antibody or antigen-binding fragment thereof is separated by 10-20 days, optionally 12-18 days. In certain embodiments each dose of anti-CD70 antibody is separated by 14-17 days.

The BCL-2 inhibitor, preferably venetoclax or pharmaceutically acceptable salt thereof, of the combination may be dosed according to any regimen determined to be effective for the compound. The FDA prescribing information for use of Venclexta® in treating AML proposes a dosing schedule having a ramp-up phase followed by a maintenance phase. In situations where Venclexta® is prescribed in combination with azacitidine or decitabine, a dosing schedule is recommended consisting of: 100 mg Venclexta® on day 1; 200 mg Venclexta® on day 2; 400 mg Venclexta® on day 3; and 400 mg Venclexta® in combination with 75 mg/m$^2$ azacitidine or 20 mg/m$^2$ decitabine daily thereafter until disease progression or unacceptable toxicity is observed. In situations where Venclexta® is prescribed in combination with low-dose cytarabine, a dosing schedule is recommended consisting of: 100 mg Venclexta® on day 1; 200 mg Venclexta® on day 2; 400 mg Venclexta® on day 3; and 600 mg Venclexta® in combination with 20 mg/m$^2$ daily thereafter until disease progression or unacceptable toxicity is observed.

In certain embodiments, each dose, for example oral dose, of the venetoclax or pharmaceutically acceptable salt thereof is in the range from 100 mg-600 mg. In certain embodiments, the venetoclax or pharmaceutically acceptable salt thereof is dosed daily at 400 mg. In certain embodiments, the venetoclax or pharmaceutically acceptable salt thereof is dosed daily at 600 mg. As described above, the daily fixed-dosing of venetoclax may be preceded by a ramp-up period, for example 3 days, wherein increasing doses of venetoclax are administered to the patient until the maintenance daily dose is reached.

For embodiments of the invention wherein the combination comprises a nucleoside metabolic inhibitor or the method comprises administering a nucleoside metabolic inhibitor, the nucleoside metabolic inhibitor may be administered at a dose in the range of 20-100 mg/m$^2$ per day. As already noted, ranges described herein include the end points of the range unless indicated otherwise—for example, administration at a dose in the range of 20-100 mg/m$^2$ per day includes administration at a dose of 20 mg/m$^2$ per day and administration at a dose of 100 mg/m$^2$ per day, as well as all doses between the two end points.

In certain embodiments, the nucleoside metabolic inhibitor is azacitidine and is administered at a dose in the range of 70-80 mg/m$^2$ per day. In certain preferred embodiments the nucleoside metabolic inhibitor is azacitidine and is administered at a dose of 75 mg/m$^2$ per day.

In certain embodiments, the nucleoside metabolic inhibitor is decitabine and is administered at a dose in the range of 15-25 mg/m$^2$ per day. In certain preferred embodiments the nucleoside metabolic inhibitor is decitabine and is administered at a dose of 20 mg/m$^2$ per day.

For embodiments wherein the combination of the invention includes a nucleoside metabolic inhibitor or the method involves administration of a nucleoside metabolic inhibitor, the nucleoside metabolic inhibitor may be administered over a dosing period of a daily dose for 5-10 days. That is, a dose of the nucleoside inhibitor is administered every day for a period or 5, 6, 7, 8, 9, or 10 days in length. In certain preferred embodiments the nucleoside metabolic inhibitor is administered over a dosing period of a daily dose for 7 days. The preferred nucleoside metabolic inhibitor is azacitidine.

In certain embodiments, the nucleoside metabolic inhibitor is administered according to a dosage regimen of repeated dosing periods, wherein the end of one dosing period and the start of the next dosing period are separated by 18-25 days. That is, the dosage regimen includes at least 2 dosing periods in which a dose of the nucleoside inhibitor is administered every day (for example for a period 5, 6, 7, 8, 9 or 10 days in length), wherein the end of the one dosing period and the start of the next dosing period are separated by 18, 19, 20, 21, 22, 23, 24, or 25 days. In certain embodiments the end of one dosing period and the start of the next dosing period are separated by 21 days.

In certain embodiments, each dosing period is of the same length (e.g. 7 days). In certain embodiments, the end of each dosing period and the start of the next dosing period are separated by the same number of days (e.g. 21 days).

In certain embodiments, the first dose of nucleoside metabolic inhibitor is administered 7-21 days after the first dose of CD70 antibody or antigen binding fragment thereof. In certain embodiments the first dose of nucleoside metabolic inhibitor is administered 10-17 days after the first dose of CD70 antibody or antigen binding fragment thereof. In certain embodiments the first dose of nucleoside metabolic inhibitor is administered 14 days after the first dose of CD70 antibody or antigen binding fragment thereof.

In certain embodiments, one of the daily doses of the nucleoside metabolic inhibitor is administered on the same day as a dose of the CD70 antibody or antigen binding fragment thereof. That is, in embodiments of the methods of the invention in which the subject is administered both a CD70 antibody (or antigen binding fragment thereof) and a nucleoside metabolic inhibitor, the dosage regimes of both the CD70 antibody and the nucleoside metabolic inhibitor are such that at least one of the scheduled doses of the CD70 antibody is on the same day as one of the scheduled daily doses of the nucleoside metabolic inhibitor. That day could be the first, second, third, fourth, fifth, sixth or seventh day of the dosing period of the nucleoside metabolic inhibitor.

In certain embodiments, a dose of the CD70 antibody or antigen binding fragment thereof is administered every 14-17 days and the nucleoside metabolic inhibitor is administered according to a dosage regimen of repeated dosing periods of a daily dose for 7 days, wherein the end of one dosing period and the start of the next dosing period are separated by 21 days, and wherein the first daily dose of the first dosing period is administered 14 days after the first dose of the anti-CD70 antibody or antigen-binding fragment thereof.

In certain embodiments, one patient treatment cycle consists of 28 days and the nucleoside metabolic inhibitor, preferably azacitidine or decitabine, is administered every day for a period of 5, 6, 7, 8, 9 or 10 days beginning on day 1 of the cycle. The methods of treatment described herein may comprise multiple treatment cycles. Each treatment cycle may replicate the preceding treatment cycle. In certain embodiments, a patient treated with a CD70 antibody, a BCL-inhibitor (preferably venetoclax or a pharmaceutically acceptable salt thereof) and azacitidine is treated according to a cycle consisting of 28 days wherein azacitidine is administered daily on the first 7 days of the 28-day cycle. In certain embodiments, a patient treated with a CD70 antibody, a BCL-inhibitor (preferably venetoclax or a pharmaceutically acceptable salt thereof) and decitabine is treated according to a cycle consisting of 28 days wherein decitabine is administered daily on the first 5 days of the 28-day cycle. For embodiments wherein the patient is treated according to a 28-day cycle with a CD70 antibody, a BCL-inhibitor ((preferably venetoclax or a pharmaceutically acceptable salt thereof) and a nucleoside metabolic inhibitor (preferably azacitidine or decitabine), the CD70 antibody may be administered on day 3 and/or day 17 of the 28-day cycle. In preferred embodiments, the CD70 antibody is ARGX-110. In further preferred embodiments, the CD70 antibody (for example ARGX-110) is administered at a dose of 10 mg/kg.

It is a further advantage of the invention that following an initial period of combination therapy, the administration of an NMI (e.g. azacitidine) can be tapered or stopped. There is the potential for accumulated toxicity arising from prolonged periods of NMI treatment, for example cytopenias arising from the effect of NMIs on non-blast cell types. Therefore, by tapering or stopping the dose of NMI after an initial period, the risk of such toxicity will be reduced and non-blast cell types can recover. In certain embodiments, treatment according to the invention comprises administering to the patient a CD70 antibody, a BCL-2 inhibitor (for example venetoclax) and a NMI as a combination therapy according to any of the embodiments described above in a first stage (induction therapy), and in a subsequent second stage administering to the patient a CD70 antibody, a BCL-2 inhibitor (for example venetoclax) and a NMI as a combination therapy but wherein the dose of the NMI in the second stage (maintenance therapy) is lower than the dose of NMI administered in the first stage. The dose of the NMI in the second stage may be zero.

In such embodiments, the dose of CD70 antibody administered in the second stage (i.e. maintenance therapy) is any dose according to the embodiments already described. That is, in certain embodiments the dose is in the range from 0.1 mg/kg to 25 mg/kg, for example 0.1 mg/kg to 20 mg/kg, for example from 1 mg/kg to 20 mg/kg. In certain embodiments the dose is in the range of from 0.1 mg/kg to 15 mg/kg per dose. In certain embodiments the dose is in the range from 0.5 mg/kg to 2 mg/kg. In certain embodiments the dose is 1 mg/kg, 3 mg/kg, 10 mg/kg, or 20 mg/kg. In certain embodiments the dose is 1 mg/kg. In certain embodiments the dose is 10 mg/kg.

The duration of the first stage (i.e. induction therapy), the timing of the transition to the second stage (i.e. maintenance therapy) and the extent to which the dose of NMI is tapered or stopped entirely are factors that will be tailored to the individual patient and determined by their clinician according to the individual patient's response to therapy and their medical history. Therefore the following embodiments are provided by way of non-limiting example. In certain embodiments the induction therapy is administered to the patient until their bone marrow and/or peripheral blood blast percentage is less than 10%, optionally less than 5%. In certain embodiments, the induction therapy is administered for at least 5 NMI dosing periods, optionally at least 6, 7, 8, 9, or at least 10 NMI dosing periods.

In certain embodiments, the dose of the NMI in the maintenance period is no more than 50 $mg/m^2$ per day, optionally no more than 40 $mg/m^2$ per day, optionally no more than 30 $mg/m^2$ per day, optionally no more than 20 $mg/m^2$ per day. In certain embodiments, the dose of the NMI in the maintenance period is zero.

As explained elsewhere herein, the agents of the combinations may be formulated for administration by any suitable routes of administration. Thus, the administration of the agents in accordance with the methods of the invention can be via any suitable routes and need not be via the same route for individual agents. For example, the CD70 antibody or antigen binding fragment thereof may be administered intravenously whilst the BCL-2 inhibitor (e.g. venetoclax) is administered orally. For embodiments wherein the patient or subject receives a hypomethylating agent such as azacitidine or decitabine, such agent may be administered intravenously or subcutaneously via injection.

Treatment Outcomes

In certain embodiments, the methods described herein involve monitoring the patient's blast count i.e. the number of blast cells. As used herein, "blast cells" or "blasts" refer to myeloblasts or myeloid blasts which are the myeloid progenitor cells within the bone marrow. In healthy individuals, blasts are not found in the peripheral blood circulation and there should be less than 5% blast cells in the bone marrow. In subjects with myeloid malignancies, particularly AML and MDS, there is increased production of abnormal blasts with disrupted differentiation potential, and the overproduction of these abnormal blasts can be detected by monitoring the patient's blast count in the peripheral blood circulation or the bone marrow or both.

The proportion of blast cells in the bone marrow or peripheral blood can be assessed by methods known in the art, for example flow cytometric or cell morphologic assessment of cells obtained from a bone marrow biopsy of the subject, or a peripheral blood smear. The proportion of blasts is determined versus total cells in the sample. For example, flow cytometry can be used to determine the proportion of blast cells using the number of $CD45^{dim}$, $SSC^{low}$ cells relative to total cell number. By way of further example, cell morphological assessment can be used to determine the number of morphologically identified blasts relative to the total number of cells in the field of view being examined.

In certain embodiments are provided methods for reducing the proportion of blasts cells in the bone marrow to less than 25%, less than 20%, for example less than 10%. In certain embodiments are provided methods for reducing the proportion of blasts cells in the bone marrow to less than 5%. In certain embodiments are provided methods for reducing the proportion of blast cells in the bone marrow to between about 5% and about 25%, wherein the bone marrow blast cell percentage is also reduced by more than 50% as compared with the bone marrow blast cell percentage prior to performing the method (or pretreatment).

In certain embodiments are provided methods for reducing the proportion of blasts cells in the peripheral blood to less than 25%, less than 20%, for example less than 10%. In certain embodiments are provided methods for reducing the proportion of blasts cells in the peripheral blood to less than 5%. In certain embodiments are provided methods for reducing the proportion of blast cells in the peripheral blood to between about 5% and about 25%, wherein the peripheral blood blast cell percentage is also reduced by more than 50% as compared with the peripheral blast cell percentage prior to performing the method (or pretreatment).

For clinical determination of blast cell percentage, typically cell morphological (also known as cytomorphology) assessment is preferred.

In particular embodiments, the methods described herein induce a complete response. In the context of AML treatment, a complete response or "complete remission" is defined as: bone marrow blasts<5%; absence of circulating blasts and blasts with Auer rods; absence of extramedullary disease; ANC≥$1.0\times10^9$/L (1000 μL); platelet count≥$100\times10^9$/L (100,000 μL), see Döhner et al. (2017) Blood 129(4): 424-447.

The methods may achieve a complete response with platelet recovery i.e. a response wherein the platelet count is >$100\times10^9$/L (100,000/μL). The methods may achieve a complete response with neutrophil recovery i.e. a response wherein the neutrophil count is >$1.0\times10^9$/L (1000/μL). Alternatively or in addition, the methods may induce a transfusion independence of red blood cells or platelets, or both, for 8 weeks or longer, 10 weeks or longer, 12 weeks or longer.

In particular embodiments, the methods described herein induce a minimal or measurable residual disease (or MRD) status that is negative, see Schuurhuis et al. (2018) Blood. 131(12): 1275-1291.

In certain embodiments, the methods described herein induce a complete response without minimal residual disease ($CR_{MRD-}$), see Döhner et al. ibid.

The method may achieve a partial response or induce partial remission. In the context of AML treatment, a partial response or partial remission includes a decrease of the bone marrow blast percentage of 5% to 25% and a decrease of pretreatment bone marrow blast percentage by at least 50%, see Döhner et al. ibid.

The methods described herein may increase survival. The term "survival" as used herein may refer to overall survival, 1-year survival, 2-year survival, 5-year survival, event-free survival, progression-free survival. The methods described herein may increase survival as compared with the gold-standard treatment for the particular disease or condition to be treated. The gold-standard treatment may also be identified as the best practice, the standard of care, the standard medical care or standard therapy. For any given disease, there may be one or more gold-standard treatments depending on differing clinical practice, for example in different countries. The treatments already available for myeloid malignancies are varied and include chemotherapy, radiation therapy, stem cell transplant and certain targeted therapies. Furthermore, clinical guidelines in both the US and Europe govern the standard treatment of myeloid malignancies, for example AML, see O'Donnell et al. (2017) Journal of the National Comprehensive Cancer Network 15(7):926-957 and Döhner et al. (2017) Blood_129(4):424-447, both incorporated by reference.

The methods of the present invention may increase or improve survival relative to patients undergoing any of the standard treatments for myeloid malignancy.

The methods described herein may include a further step of subjecting the patient or subject to a bone marrow transplant. The methods described herein may also be used to prepare a patient or subject having a myeloid malignancy for a bone marrow transplantation. As described above, the methods of the present invention may be carried out so as to reduce the absolute or relative numbers of blast cells in the bone marrow or peripheral blood. In certain embodiments, the methods are carried out so as to reduce the blast cell count in the bone marrow and/or peripheral blood prior to transplant. The methods may be used to reduce the blast cell count to less than 5% to prepare the patient or subject for a bone marrow transplant.

D. Kits

The combinations of the invention described herein may be provided in the form of a kit packaged so as to include instructions for use.

Incorporation by Reference

Various publications are cited in the foregoing description and throughout the following examples, each of which is incorporated by reference herein in its entirety.

EXAMPLES

In a recent Phase 1 clinical trial, treatment of older and unfit AML patients with the ADCC-enhanced humanized monoclonal anti-CD70 antibody (mAb) cusatuzumab (also referred to herein as ARGX-110) in combination with HMA demonstrated promising clinical activity and a favorable tolerability profile.

The BCL-2 antagonist, venetoclax, targets and eliminates leukemic stem cells (LSCs) by suppression of oxidative phosphorylation and demonstrated very promising activity in older AML patients in clinical phase I and II studies in combination with standard of care (Pollyea et al., *Nature Medicine* (2018) 24; 1859-1866). However, even with novel agents such as venetoclax, there are still patients that become refractory or relapse. It was hypothesized that combining venetoclax and cusatuzumab with distinct but complementary mechanisms of action could successfully eliminate LSCs.

Methods

To test this hypothesis, a drug-combination study was carried out according to the Chou-Talalay method (Chou T C, *Cancer Research* (2010) 70(2); 440-6) in CD70-expressing AML cell lines such as MOLM-13, NB-4, and NOMO-1 cells in vitro. MOLM-13 AML cells express FLT3-ITD and NOMO-1 cells express t(9;11)(p22;q23). Each of these genetic aberrations conveys a poor prognosis to patient outcome. NB-4 is an acute promyelocytic leukemia (APL) cell line, where APL is a subset of AML patients. Of note, NOMO-1 and MOLM-13 cells express high levels of CD70 as measured at the mRNA and protein levels. The MOLM-13 AML cells also express BCL-2 and are sensitive to BCL-2 inhibition (Lin et al. *Scientific Reports*(2016) 6; 27696).

MOLM-13 (Matsuo et al., *Leukemia* (1997) 11(9): 1469-77), NOMO-1 (Kato et al., *Acta Haematol Jpn,* 1986), MV4-11 and NB4 (Lanotte et al., *Blood* (1991) 77(5); 1080-86) cells were purchased from ATCC. The cell lines were tested mycoplasma-free and were grown in FCS-containing medium recommended by ATCC with Gluta-MAX supplement, 100 U/mL penicillin, and 100 µg/mL of streptomycin in a humidified atmosphere of 95% air and 5% $CO_2$ at 37° C.

Initially, cells from each AML cell line were treated with decitabine, cusatuzumab or venetoclax alone to determine the $IC_{50}$ for each treatment. $10^5$ AML cells were treated with a concentration range of cusatuzumab (0.1, 1.0 and 10 µg/ml), venetoclax (0.5 and 200 nM), decitabine (0.01-1 µM) or vehicle in the presence of CFSE-labelled NK cells derived from healthy individuals (ratio 1:1). The assay was performed in triplicate.

The $IC_{50}$ determination identified the following working concentrations for the subsequent synergy experiments:
1) $IC_{50}$s, MOLM-13: (decitabine:0.01 nM, venetoclax: 0.42 nM, cusatuzumab: 0.68 µg/ml)
2) $IC_{50}$s, NOMO-1: (decitabine: 0.001 nM, venetoclax: 3.4 nM, cusatuzumab: 0.14 µg/ml)
3) $IC_{50}$s, NB4: (decitabine: 4.8 nM, venetoclax: 17.3 nM, cusatuzumab: 0.3 µg/ml)
4) $IC_{50}$s, MV4-11: (decitabine: 2.36 nM, venetoclax: 5 nM, cusatuzumab: 1.2 µg/ml)

To determine synergy, a constant combination ratio experiment was carried out at equipotency ratio ($IC_{50_1}$/$IC_{50_2}$, or $IC_{50_1}$/$IC_{50_2}$/$IC_{50_3}$) so that each drug contributed equally to cell killing. Combination drug dose responses were assessed in two technical replicates for every dose/dose combination as previously described (Riether et al., *Sci Transl Med* (2015) 7(298); 298ra119.

NOMO-1, MOLM-13, NB-4 or MV4-11 AML cell lines were treated with vehicle, decitabine, cusatuzumab or venetoclax alone, a double combination of venetoclax and decitabine, decitabine and cusatuzumab, or venetoclax and cusatuzumab, or a triple combination of decitabine, cusatuzumab and venetoclax. All combinations were tested at three high and three low concentrations (above and below the identified $IC_{50}$s) and in a constant ratio. Cells were cultured in the presence of CFSE-labeled NK cells (ratio 1:1). Viable AML cell numbers were assessed 72 hours later by Annexin V staining, and the effect of drug treatment was calculated as the ratio of surviving cells to vehicle-treated cells.

The Combination Index (CI) was calculated and plotted against Fraction affected (Fa) using CompuSyn software. The resultant plot of the combination index (CI) against fraction affected (Fa) for all combinations is shown in FIG. 1, with the individual combinations shown in FIGS. 2A-2D.

Fa values of 0, 0.5, and 1 correspond to 0, 50, and 100% killed cells. A CI of <1, 1, >1 represents synergism, additivity, and antagonism, respectively. $IC_{50}$s indicates Fa values reached for the combination of respective $IC_{50}$ concentrations. The principles and advantages of the Fa-CI plot method of assessing synergism are provided in, for example, Chou T C, *Cancer Research* (2010) 70(2); 440-6 and Zhao et al. *Front Biosci (Elite Ed).* (2010) 2; 241-249 (each of which is incorporated herein by reference in its entirety).

In addition, the effect of the cusatuzumab/venetoclax and the cusatuzumab/venetoclax/HMA combination was tested on primary LSCs from AML patients. Primary CD34$^+$CD38$^-$ leukemic stem cells (LSCs) were isolated from newly-diagnosed AML patients and treated with cusatuzumab, decitabine, or venetoclax monotherapy or in combination. The effect on colony formation and re-plating capacity of the LSCs was then assessed.

Specifically, CD34$^+$CD38$^-$ AML LSCs from three AML patients (P1, P2 and P3) were cultured overnight in the presence of NK cells (ratio 1:1) with cusatuzumab (Cusa: 0.3 µg/ml) or venetoclax (Ve: 6 nM) as monotherapy or in combination overnight in duplicates followed by plating in methylcellulose. CD34$^+$CD38$^-$ AML LSCs from two further AML patients (P4 and P5) were cultured overnight in the presence of NK cells (ratio 1:1) with cusatuzumab (Cusa: 0.3 µg/ml), decitabine (0.01 µM), or venetoclax (Ve: 6 nM) as monotherapy or in combination. Colony formation was assessed 14 days later.

Results

1. Cusatuzumab Used in Combination with Venetoclax and/or Decitabine Demonstrated Synergy in the Elimination of AML Cell Lines In Vitro Venetoclax and/or decitabine in combination with cusatuzumab synergistically eliminated CD70-expressing NOMO-1 AML cells in a broad dose range (see FIG. 1 and FIG. 2B-2D).

At the higher effect levels (Fa>0.7), which are more relevant in tumor killing (Chou, 2010), the combinations demonstrated strong synergy. Importantly, the CI of the venetoclax and cusatuzumab (Ven/Cusa) and venetoclax, cusatuzumab and decitabine (Ven/Cusa/Dec) were approaching 0.1, indicating very strong synergy. Venetoclax and decitabine (Ven/Dec) and cusatuzumab and decitabine (Cusa/Dec) also achieved synergy at higher effect levels, with a maximal CI~0.5. The synergistic effect of the Ven/Cusa combination was similar to the synergistic effect observed for Ven/Cusa/Dec combination.

Similar results were observed in the NB4 and MV4-11 AML cell lines, with all cusatuzumab combinations exhibiting potent synergy at high effect levels (Fa>0.5) (see FIGS. 3A-3D and FIG. 5).

In the MOLM-13 cell line, all double combinations showed a synergistic effect at lower effect levels. Venetoclax/decitabine and cusatutzumab/decitabine showed a synergy only at drug concentrations below a Fa of 0.4 and 0.6, respectively. At higher effect levels (Fa~0.7 to 0.8), which are more relevant in tumor killing, the combination of cusatutzumab/venetoclax demonstrated strong synergy (see FIGS. 4A-4D), though some antagonism was observed at the highest effect levels. The triple combination of venetoclax, decitabine and cusatuzumab showed low levels of antagonism at all effect levels.

2. Cusatuzumab Used in Combination with Venetoclax and/or Decitabine Demonstrated Synergy in the Elimination of Primary Human AML Leukemic Stem Cells (LSCs) In Vitro To assess the effect of the cusatuzumab/venetoclax combination on primary human AML LSCs, $CD34^+$ $CD38^-$ LSCs from five AML patients were treated (P1-P5). The patient characteristics are shown below.

TABLE 2

Patient characteristics P1-P5

| ID | Age (y) | Sex | FAB | Risk | Cytogenetics | Mutations |
|---|---|---|---|---|---|---|
| 1 | 72 | M | M4 | Int. | NK | ASXL1, DNMT3A, IDH2, SRSF2 |
| 2 | 62 | M | M4 | Adv. | Monosomy 7 | — |
| 3 | 50 | M | M2 | Adv. | del(16), t(11;16), trisomy 14 | IDH2, DNMT3A |
| 4 | 75 | M | Sec. AML. | Int. | NK | DNMT3a, U2AF1 |
| 5 | 80 | F | M2 | Adv. | NK | FLT3-ITD |

The results for patients P1, P2 and P3 are shown in FIGS. 6A-6B and FIGS. 7A-7B. FIG. 6 shows the absolute numbers of colonies formed per well following treatment, indicative of the number of LSCs. FIG. 7 shows the same data expressed as a ratio of the mean colonies per well for the vehicle treated group for each patient.

Figure 6A:
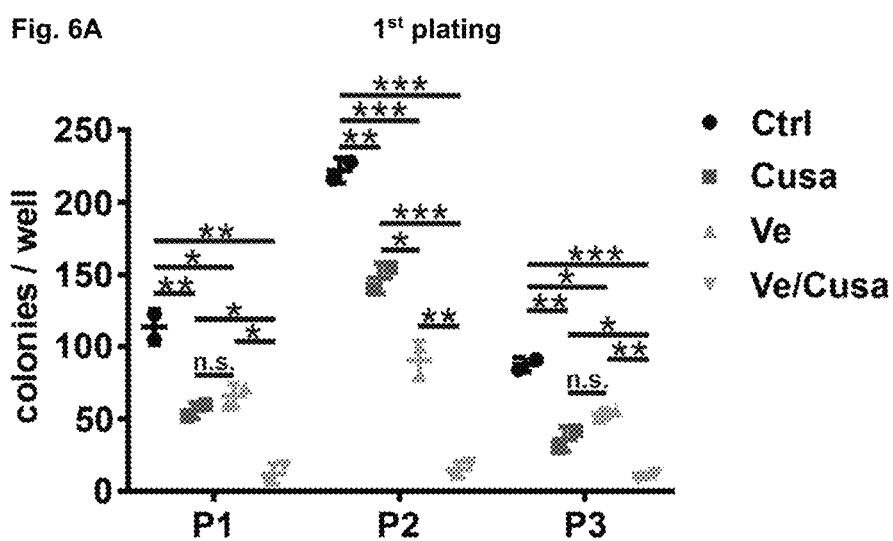
FIGS. 6A-6B: Combined venetoclax and cusatuzumab treatment synergistically eliminates leukemic stem cells (LSCs) in vitro. $CD34^+CD38^-$ AML LSCs from patients P1-3 were cultured with cusatuzumab (Cusa: 0.3 µg/ml) or venetoclax (Ve: 6 nM) alone or in combination in the presence of NK cells (ratio 1:1) overnight in duplicates followed by plating in methylcellulose. Colony formation was assessed 14 days later.

FIGS. 6 and 7 show that the synergistic effect between cusatuzumab and venetoclax observed in the AML cell lines translated into a potent and significant reduction in the number of LSCs compared to either treatment alone (FIG. 6A and FIG. 7A).

Figure 6B:
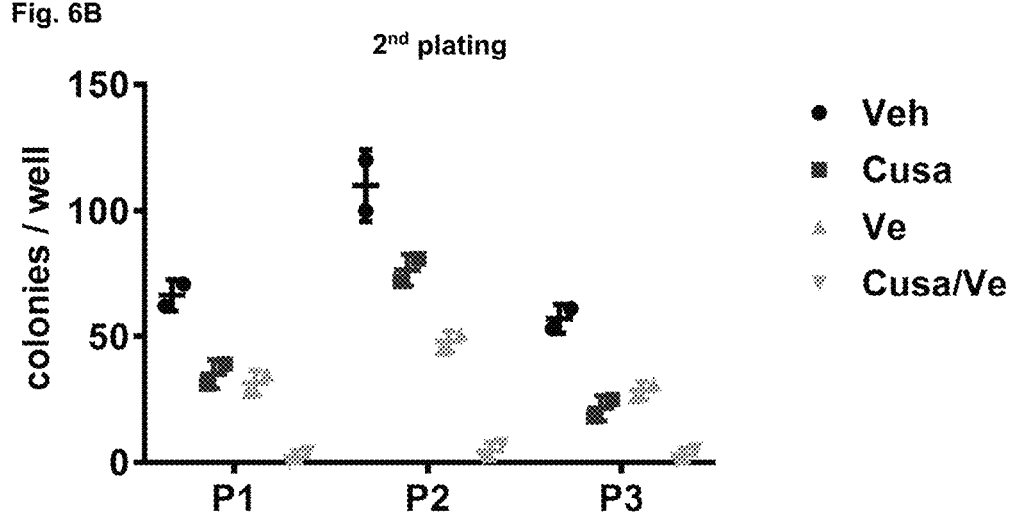

FIGS. 6B and 7B show that the effect of reducing LSC numbers was maintained when the first colonies were re-plated in the absence of the treatment molecules.

Figure 8A:
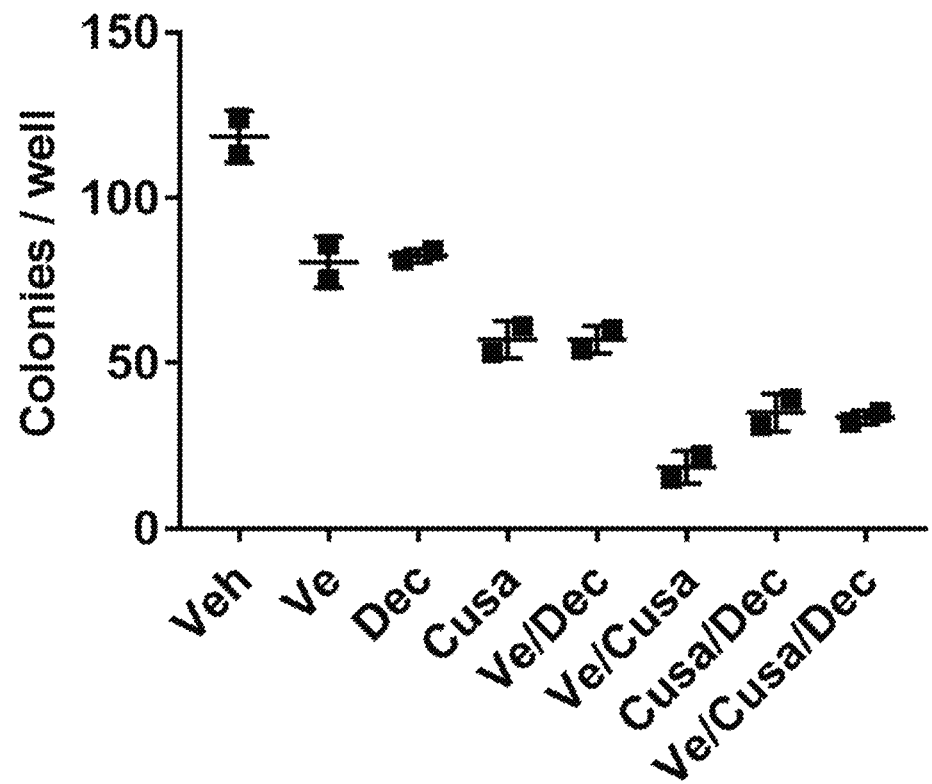
FIGS. 8A-8B: Combined venetoclax and cusatuzumab treatment synergistically eliminates LSCs in vitro. $CD34^+CD38^-$ AML LSCs from patients P4 and P5 were cultured with cusatuzumab (Cusa: 0.3 µg/ml), venetoclax (Ve: 6 nM) or decitabine (0.01 µM) alone or in combination in the presence of NK cells (ratio 1:1) overnight in duplicates followed by plating in methylcellulose. Colony formation was assessed 14 days later. Data are represented as mean±S.D (FIG. 8A) Results from a single patient.
Figure 8B:
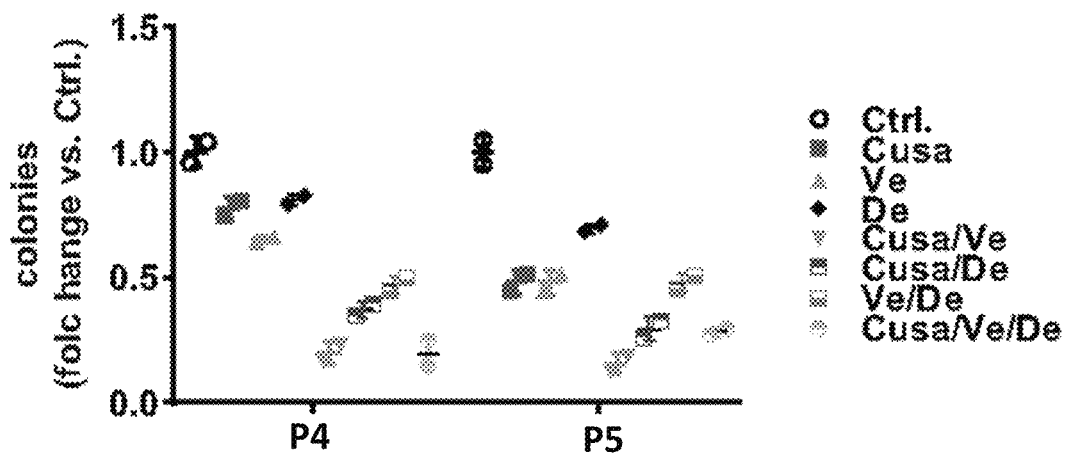

The results for patients P4 and P5 are shown in FIGS. 8A-8B. In these patients, the triple combination of cusatuzumab, decitabine and venetoclax showed equivalent efficacy to the dual combination of cusatuzumab and venetoclax. This is in line with the fact that no increase in synergy was observed for the triple combination compared to the Ven/Cusa combination (FIG. 1).

3. Venetoclax Increased CD70 Expression

Figure 9:
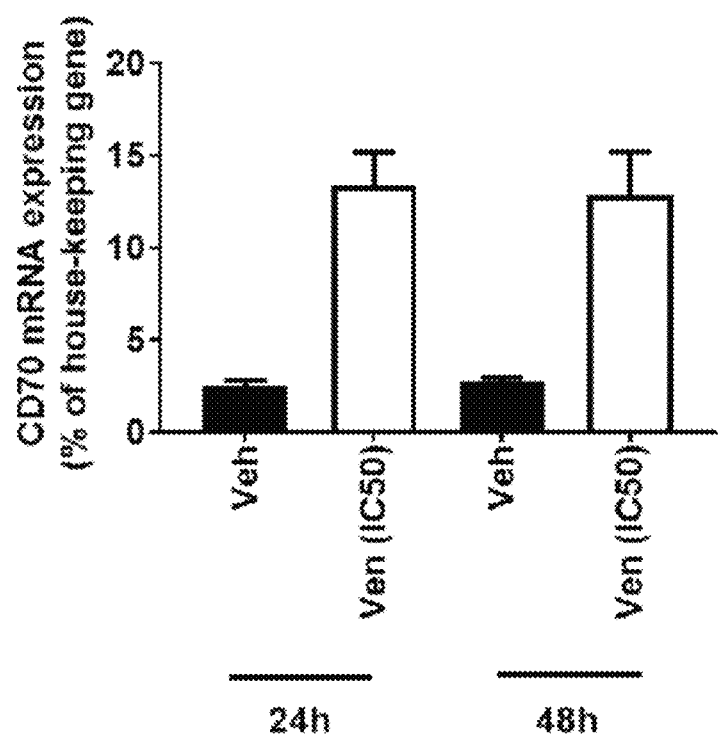
FIG. 9: CD70 mRNA expression (as percentage of housekeeping gene) following treatment with vehicle (Veh) or venetoclax (Ven) for 24 or 48 hrs.
Figure 10:
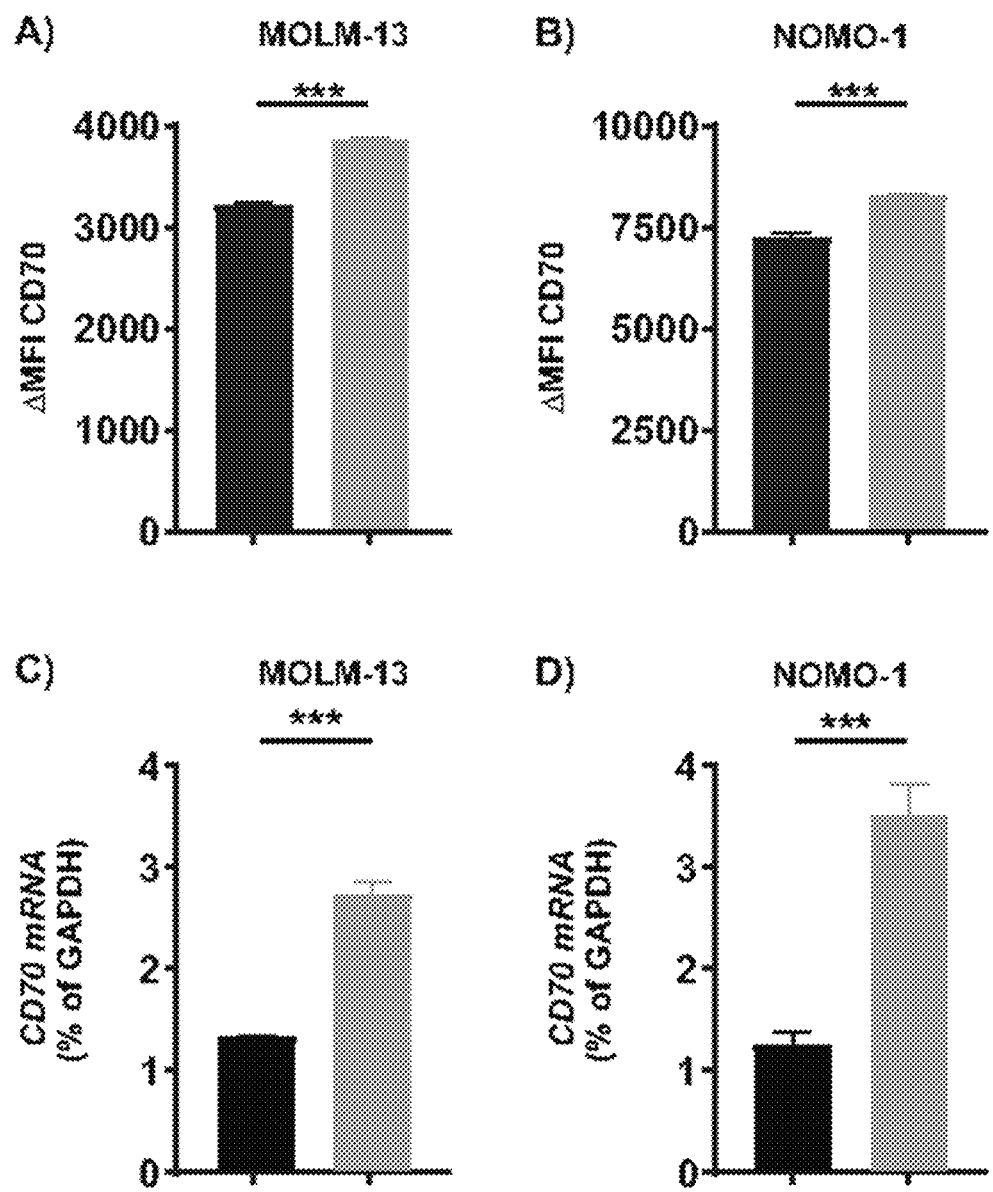
FIG. 10: CD70 protein and mRNA expression by MOLM-13 and NOMO-1 cells in the presence (gray bars) and absence (black bars) of venetoclax. Significance was determined using a Student's t-test. MFI=mean fluorescence intensity. *** $P<0.001$.

The effect of venetoclax on expression of CD70 at both the mRNA and protein level was assessed. The results are shown in FIG. 9 and FIG. 10, and clearly demonstrate that CD70 expression was up-regulated in AML cells in the presence of venetoclax.

CONCLUSIONS

The present experiments were performed to determine whether combination therapy with cusatuzumab and venetoclax and/or a hypomethylating agent (e.g. azacitidine or decitabine) could provide effective treatment for AML greater than each monotherapy alone. It was further explored whether the combination treatments could exhibit synergistic therapeutic effects.

The Combination Index (CI) provided by the Chou-Talalay method is an established means for determining whether drug combinations interact in a synergistic, additive or antagonistic manner. It was hypothesised that venetoclax and cusatuzumab may act in a synergistic manner since mechanistically it could be shown that treatment with venetoclax results in up-regulation of CD70 on AML cells (FIGS. 9 and 10). This could mean that venetoclax renders LSCs more susceptible to cytolytic killing with cusatuzumab. However, as noted in Chou 2010 (Chou *Cancer Res.* (2010) January 15; 70(2):440-6, incorporated herein by reference), synergistic effects between drugs are hard to predict, even in cases where there is some knowledge of the mechanism by which each individual drug acts.

The data presented in FIGS. 1-5 demonstrate that the Ven/Cusa combination exhibited a strong synergistic effect against AML cells, especially at high effect levels. The potent synergy was maintained for the triple combination further including decitabine as a hypomethylating agent.

This synergy is particularly advantageous since this indicates that, when the drugs are in combination, significantly lower concentrations of each drug can be used compared to the concentrations required to achieve the same effect as monotherapies.

Because the cell line experiments exhibited a strong synergistic effect of the venetoclax/cusatuzumab combination, the combination was tested on primary AML LSCs. Primary LSCs provide a rigorous and more clinically relevant assessment of potential therapeutic benefit, as these cells drive the aberrant proliferation characteristic of AML. The synergistic effect of the Ven/Cusa combination therapy observed in the cell lines translated to a potent reduction of primary AML leukemic stem cells (LSCs) from human patients (FIGS. 6-8). These data demonstrate that for all patient samples the combination therapy inhibited LSC colony formation to an extent significantly greater than either therapy alone. The data appear to show a synergy between the components of the Ven/Cusa combination. (Due to the low numbers of primary cells available, it was not feasible to test the synergistic effect using the Chou-Talalay method).

When the effect of the cusatuzumab/venetoclax treatment on LSC function was analyzed in a more stringent way by serial re-plating experiments in vitro, the impaired colony formation after combination treatment observed after the first plating was maintained during subsequent the re-plating. This was the case even though cusatuzumab and venetoclax were not present in the re-plating, indicating an effective reduction of LSCs and their proliferative potential.

The triplet combination cusatuzumab/venetoclax/decitabine reduced colony and re-plating capacity of primary human LSCs to the same extent as the cusatuzumab/venetoclax combination treatment. It may be, therefore, that effective treatment of AML can be achieved using the combination of cusatuzumab and venetoclax without the need to include a HMA such as decitabine, thereby reducing the exposure of the patient to toxic therapies.

The invention claimed is:

1. A method for treating a malignancy in a human subject, said method comprising administering to the subject an effective amount of a combination comprising
   (i) an antibody or antigen binding fragment thereof that specifically binds to CD70, comprising a heavy chain variable domain (VH) comprising the CDRH1, CDRH2, and CDRH3 amino acid sequences of the VH amino acid sequence of SEQ ID NO: 4 and a light chain variable domain (VL) comprising the CDRL1, CDRL2, and CDRL3 amino acid sequences of the VL amino acid sequence of SEQ ID NO: 8; wherein the antibody is not an antibody drug conjugate, and
   (ii) venetoclax or a pharmaceutically acceptable salt thereof, wherein the malignancy is selected from the group consisting of acute myeloid leukemia (AML); myelodysplastic syndromes (MDS); myeloproliferative neoplasms (MPN); chronic myeloid leukemia (CML); and chronic myelomonocytic leukemia (CMML).

2. The method of claim 1, wherein
HCDR1 comprises the amino acid sequence of SEQ ID NO: 1;
HCDR2 comprises the amino acid sequence of SEQ ID NO: 2;
HCDR3 comprises the amino acid sequence of SEQ ID NO: 3;
LCDR1 comprises the amino acid sequence of SEQ ID NO: 5;
LCDR2 comprises the amino acid sequence of SEQ ID NO: 6; and
LCDR3 comprises the amino acid sequence of SEQ ID NO: 7.

3. The method of claim 1, wherein the VH comprises an amino acid sequence at least 95% identical to the amino acid sequence of SEQ ID NO: 4.

4. The method of claim 1, wherein the VL comprises an amino acid sequence at least 95% identical to the amino acid sequence of SEQ ID NO: 8.

5. The method of claim 1, wherein the VH comprises the amino acid sequence of SEQ ID NO: 4.

6. The method of claim 1, wherein the VL comprises the amino acid sequence of SEQ ID NO: 8.

7. The method of claim 1, wherein the antibody or antigen binding fragment thereof is administered at a dose in the range of 0.1-25 mg/kg.

8. The method of claim 1, wherein venetoclax is administered at a dose in the range of 100 mg-600 mg.

9. The method of claim 1, further comprising administering azacitidine to the subject.

10. The method of claim 9, wherein the azacitidine is administered at a dose of 70-80 mg/m$^2$.

11. The method of claim 1, further comprising administering decitabine to the subject.

12. The method of claim 11, wherein the decitabine is administered at a dose of 15-25 mg/m$^2$.

13. The method of claim 1, wherein the dose at which the antibody or antigen binding fragment thereof is administered and the dose at which the venetoclax is administered are each selected such that the combination provides synergistic treatment.

14. The method of claim 1, further comprising monitoring a blast count of the subject.

15. The method of claim 14, wherein the blast count of the subject is reduced to less than 5%.

16. The method of claim 14, wherein the blast count of the subject is reduced to between 5% and 25% and a blast percentage of the subject is reduced by more than 50% as compared to pretreatment.

17. The method of claim 1, which induces a partial response or a complete response to the malignancy in the subject.

18. The method of claim 17, which induces a complete response to the malignancy with platelet recovery in the subject.

19. The method of claim 17, which induces a complete response to the malignancy with neutrophil recovery in the subject.

20. The method of claim 1, which induces transfusion independence of red blood cells or platelets, or both, in the subject for 8 weeks or longer.

21. The method of claim 1, which increases survival of the subject.

22. The method of claim 1, which increases survival of the subject versus standard of care agents used for treatment of myeloid malignancies.

23. The method of claim 1, which induces a minimal residual disease status that is negative in the subject.

24. The method of claim 1, further comprising subjecting the subject to a bone marrow transplantation.

25. The method of claim 1, further comprising administering one or more additional anti-cancer agents suitable for the treatment of malignancies to the subject.

26. The method of claim 25, wherein the one or more additional anti-cancer agents are selected from agents suitable for the treatment of AML.

27. The method of claim 26, wherein the one or more additional anti-cancer agents are selected from the group consisting of selectin inhibitors; FMS-like tyrosine kinase receptor 3 (FLT3) inhibitors; cyclin-dependent kinase inhibitors; aminopeptidase inhibitors; JAK/STAT inhibitors; cytarabine; fludarabine; anthracycline compounds; doxorubicin; hydroxyurea; Vyxeos; IDH1 or IDH2 inhibitors; Smoothened inhibitors; BET bromodomain inhibitors; CD123 targeting agents; CD33 targeting agents; HDAC inhibitors; LSC targeting agents; AML bone marrow niche targeting agents; NEDD8-activating enzyme inhibitors; G-CSF; and topoisomerase inhibitors.

28. The method of claim 27, wherein
the selectin inhibitor is GMT-1271;
the FLT3 inhibitors are selected from the group consisting of midostaurin and gilteritinib;
the anthracycline compounds are selected from the group consisting of daunorubicin and idarubicin;
the IDH1 or IDH2 inhibitors are selected from the group consisting of enasidenib and ivosidenib;
the Smoothened inhibitor is glasdegib;
the NEDD8-activating enzyme inhibitor is pevonedistat; and
the topoisomerase inhibitors are selected from the group consisting of mitoxantrone, selinexor, and etoposide.

29. The method of claim 1, wherein the malignancy is a newly-diagnosed myeloid malignancy.

30. The method of claim 1, wherein the malignancy is a relapsed/refractory myeloid malignancy.

31. The method of claim 1, wherein the malignancy is AML or MDS.

32. The method of claim 1, wherein the malignancy is AML.

33. The method of claim 1, wherein the subject is a newly-diagnosed AML patient who is ineligible for standard intensive chemotherapy.

34. The method of claim 1, wherein the subject is a newly-diagnosed AML patient who is aged 75 years or older.

35. The method of claim 1, wherein subject a newly-diagnosed AML patient who has a comorbidity that precludes the use of standard invasive chemotherapy.

36. The method of claim 1, wherein the antibody is cusatuzumab.

* * * * *

SEQUENCE LISTING

<160> NUMBER OF SEQ ID NOS: 8

<210> SEQ ID NO 1
<211> LENGTH: 5
<212> TYPE: PRT
<213> ORGANISM: Artificial sequence
<220> FEATURE:
<223> OTHER INFORMATION: Synthetic peptide

<400> SEQUENCE: 1

Val Tyr Tyr Met Asn
1               5

<210> SEQ ID NO 2
<211> LENGTH: 17
<212> TYPE: PRT
<213> ORGANISM: Artificial sequence
<220> FEATURE:
<223> OTHER INFORMATION: Synthetic peptide

<400> SEQUENCE: 2

Asp Ile Asn Asn Glu Gly Gly Thr Thr Tyr Tyr Ala Asp Ser Val Lys
1               5                   10                  15

Gly

<210> SEQ ID NO 3
<211> LENGTH: 13
<212> TYPE: PRT
<213> ORGANISM: Artificial sequence
<220> FEATURE:
<223> OTHER INFORMATION: Synthetic peptide

<400> SEQUENCE: 3

Asp Ala Gly Tyr Ser Asn His Val Pro Ile Phe Asp Ser
1               5                   10

<210> SEQ ID NO 4
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
            100                 105                 110

Gly Gln Gly Thr Leu Val Thr Val Ser Ser
        115                 120

<210> SEQ ID NO 5

```
<211> LENGTH: 14
<212> TYPE: PRT
<213> ORGANISM: Artificial sequence
<220> FEATURE:
<223> OTHER INFORMATION: Synthetic peptide

<400> SEQUENCE: 5

Gly Leu Lys Ser Gly Ser Val Thr Ser Asp Asn Phe Pro Thr
1               5                   10

<210> SEQ ID NO 6
<211> LENGTH: 7
<212> TYPE: PRT
<213> ORGANISM: Artificial sequence
<220> FEATURE:
<223> OTHER INFORMATION: Synthetic peptide

<400> SEQUENCE: 6

Asn Thr Asn Thr Arg His Ser
1               5

<210> SEQ ID NO 7
<211> LENGTH: 10
<212> TYPE: PRT
<213> ORGANISM: Artificial sequence
<220> FEATURE:
<223> OTHER INFORMATION: Synthetic peptide

<400> SEQUENCE: 7

Ala Leu Phe Ile Ser Asn Pro Ser Val Glu
1               5                   10

<210> SEQ ID NO 8
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 8

Gln Ala Val Val Thr Gln Glu Pro Ser Leu Thr Val Ser Pro Gly Gly
1               5                   10                  15

Thr Val Thr Leu Thr Cys Gly Leu Lys Ser Gly Ser Val Thr Ser Asp
                20                  25                  30

Asn Phe Pro Thr Trp Tyr Gln Gln Thr Pro Gly Gln Ala Pro Arg Leu
            35                  40                  45

Leu Ile Tyr Asn Thr Asn Thr Arg His Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ala Glu Tyr Phe Cys Ala Leu Phe Ile Ser Asn
                85                  90                  95

Pro Ser Val Glu Phe Gly Gly Gly Thr Gln Leu Thr Val Leu Gly
                100                 105                 110
```